(12) United States Patent
Wang et al.

(10) Patent No.: US 8,748,475 B2
(45) Date of Patent: *Jun. 10, 2014

(54) METHODS AND COMPOSITIONS FOR TREATING LUPUS

(75) Inventors: Longgui Wang, Flushing, NY (US); Simon K. Mencher, New York, NY (US)

(73) Assignee: Natrogen Therapeutics International, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/197,164

(22) Filed: Aug. 3, 2011

(65) Prior Publication Data

US 2012/0058121 A1    Mar. 8, 2012

Related U.S. Application Data

(63) Continuation-in-part of application No. 12/972,908, filed on Dec. 20, 2010, now Pat. No. 8,563,525, which is a continuation-in-part of application No. 11/494,362, filed on Jul. 26, 2006, now Pat. No. 7,855,223, which is a continuation-in-part of application No. 10/754,547, filed on Jan. 12, 2004, now abandoned.

(51) Int. Cl.

| | | |
|---|---|---|
| *A61K 31/404* | (2006.01) | |
| *A61K 31/573* | (2006.01) | |
| *A61P 13/12* | (2006.01) | |
| *A61K 39/395* | (2006.01) | |
| *A61P 19/04* | (2006.01) | |
| *A61K 31/7056* | (2006.01) | |
| *A61K 31/519* | (2006.01) | |

(52) U.S. Cl.
USPC ............. 514/414; 514/171; 514/249; 514/43; 424/142.1

(58) Field of Classification Search
None
See application file for complete search history.

(56) References Cited

U.S. PATENT DOCUMENTS

| | | | |
|---|---|---|---|
| 2002/0132792 A1 | 9/2002 | Prien et al. | |
| 2003/0059862 A1* | 3/2003 | Ruben | 435/7.23 |

FOREIGN PATENT DOCUMENTS

| | | |
|---|---|---|
| WO | 99/30710 | 6/1999 |
| WO | 99/65884 | 12/1999 |
| WO | 03/051900 | 6/2003 |

OTHER PUBLICATIONS

A.D.A.M. Medical Encyclopedia entry on Lupus nephritis. Accessed on Dec. 14, 2012 at <http://www.ncbi.nlm.nih.gov/pubmedhealth/PMH0001512>.*
Rennard et al. (Am J Respir Care Med vol. 175 pp. 926-934, 2007).*
English translation of Office Action dated Nov. 11, 2013, for corresponding Japanese Application No. 2012-092614.

* cited by examiner

*Primary Examiner* — David J Blanchard
*Assistant Examiner* — Garen Gotfredson
(74) *Attorney, Agent, or Firm* — Rodney J. Fuller; Booth Udall Fuller, PLC

(57) ABSTRACT

The invention relates to compositions and methods for treating lupus. The methods typically comprise the step of administrating one or more compounds selected from isoindigo, indigo, indirubin, or derivatives thereof, such as, Meisoindigo and NATURA in an amount sufficient to treat the lupus; preferably by modulating cytokine expression. Preferably the compound is in an amount less than sufficient to substantially inhibit cyclin dependent kinases.

30 Claims, 10 Drawing Sheets

METHODS AND COMPOSITIONS FOR TREATING LUPUS

CROSS-REFERENCE TO RELATED APPLICATIONS

This application is a continuation-in-part of U.S. patent application Ser. No. 12/972,908, filed Dec. 20, 2010, now U.S. Pat. No. 8,563,525, which is a continuation-in-part of U.S. patent application Ser. No. 11/494,362, filed Jul. 26, 2006, now U.S. Pat. No. 7,855,223, which is a continuation-in-part of U.S. patent application Ser. No. 10/754,547, filed Jan. 12, 2004, abandoned, the contents of each of which are herein incorporated by reference for all purposes.

TECHNICAL FIELD

The invention relates to pharmaceutical compositions and methods of treating lupus. The method typically comprises administration of one or more compounds selected from isoindigo, indigo, indirubin, or derivatives thereof, such as, Meisoindigo and NATURA.

BACKGROUND OF THE INVENTION

Lupus is a chronic and prototypical systemic autoimmune disease characterized by multisystem microvascular inflammation leading to organ damage as a result of loss of tolerance to self-antigens [1-4]. Symptoms of lupus can occur in any part of the body, including the skin, heart, lungs, kidneys, joints and/or nervous system. Lupus may also be caused by a hypersensitive reaction to a medication.

The prevalence of lupus varies among geography regions and races from approximately 40 per 100,000 persons in Northern Europeans to more than 200 per 100,000 persons among blacks. In the United States, the number of patients with lupus is over 250,000 [2]. It is more frequent in African, Japanese and Chinese. The exact cause of lupus remains unknown, various factors including genetic, racial, hormonal, and environmental factors have been associated with the development of the disease [2, 5]. It is estimated that women are eight times more likely to develop either discoid or systemic lupus than men are. While the disease can people of all ages, including newborns and even the fetus, it usually develops in individuals who are 20 to 45 years old. Infections, renal failure, and cardiovascular diseases account for the majority of deaths as a result of lupus.

Although lupus is an autoimmune disease, its heterogeneous nature makes the exact mechanisms for its development unclear. There is currently no cure for lupus. Current treatments only focus on alleviating the symptoms, rather than the cause. These treatments include 1) anti-inflammatory medications (such as ibuprofen), 2) high doses of corticosteroids, and 3) immunosuppressants, such as methotrixate. While toxicities can become significant because of long-term maintenance therapy required, the disease eventually progresses to end-stage multiple organ damages and death. Although recent extensive studies have enriched our knowledge in understanding molecular pathogenesis of lupus, development of therapies for lupus has largely lagged. Despite its moderate efficacy, belimumab (Benlysta®) is the only new drug approved recently by FDA for treatment of lupus in over 50 years. Belimumab is an injectable monoclonal antibody designed to target B-lymphocyte stimulator BLyS protein, and to relieve flare-ups and pain caused by lupus, which may reduce the number of abnormal B cells thought to be a problem in lupus. Therefore, a new effective treatment of lupus is highly desired.

A need exists for a treatment for lupus that is effective and preferably treating the cause and not just the symptoms of the disease.

SUMMARY OF THE INVENTION

The invention is directed to a method of treating an animal with lupus. The method preferably comprises the step of administering to the animal in need of such treatment at least one compound selected from the group of Meisoindigo, tri-acetylated glycol-Meisoindigo (prodrug), or NATURA, wherein the composition is administered in an amount sufficient to treat lupus. Advantageously, the method may also be used to treat an animal with nephritis. In a preferred embodiment, the amount of compound administered is sufficient to inhibit pro-inflammatory cytokine expression and/or stimulate anti-inflammatory cytokine expression, but less than sufficient to substantially inhibit cyclin dependent kinases.

Preferably, the compound is administered in an amount sufficient to inhibit at least one of IL-1$\alpha$, $\beta$, IL-2, IL-3, IL-6, IL-7, IL-9, IL-12, IL-17, IL-18, TNF-$\alpha$, LT, LIF, Oncostatin, or IFNc1$\alpha$, $\beta$, $\gamma$. In another embodiment, the compound is administered in an amount sufficient to stimulate at least one of IL-4, IL-10, IL-11, W-13 or TGF$\beta$. And in a most preferred embodiment, the compound is administered in an amount sufficient to modulate cytokines TNF-$\alpha$, IL-1$\beta$, IL-6, and IL-10. Advantageously, the compound may be administered in an amount sufficient to reduce proteinuria levels and/or modulate a humoral response.

Quantitatively, the amount administered is preferably less than 0.36 mmol/kg per day, and preferably between 0.036 mmol/kg and 0.288 mmol/kg per day. When the compound administered is Meisoindigo, the amount administered is preferably less than 100 mg/kg per day, and more preferably between 10 mg/kg and 80 mg/kg per day.

In an alternative embodiment, the method comprises the step of administering a first and second compound to an animal in need of treatment for lupus. Preferably, the first compound is Meisoindigo, tri-acetylated glycol-Meisoindigo (prodrug), or NATURA, and the second compound is selected from the group consisting an anti-inflammatory agent, corticosteroid, immune suppressant, or biologic drug.

The invention also pertains to a composition for treating lupus and/or nephritis. These composition typically comprise an active compound, an agent, and a pharmaceutically acceptable carrier. In this embodiment, the active compound is selected from the group consisting of Meisoindigo, tri-acetylated glycol-Meisoindigo (prodrug), or NATURA, and the agent is selected from the group consisting of an anti-inflammatory agent, corticosteroid, immune suppressant, or biologic drug.

DETAILED DESCRIPTION OF THE PREFERRED EMBODIMENTS

Figure 1:
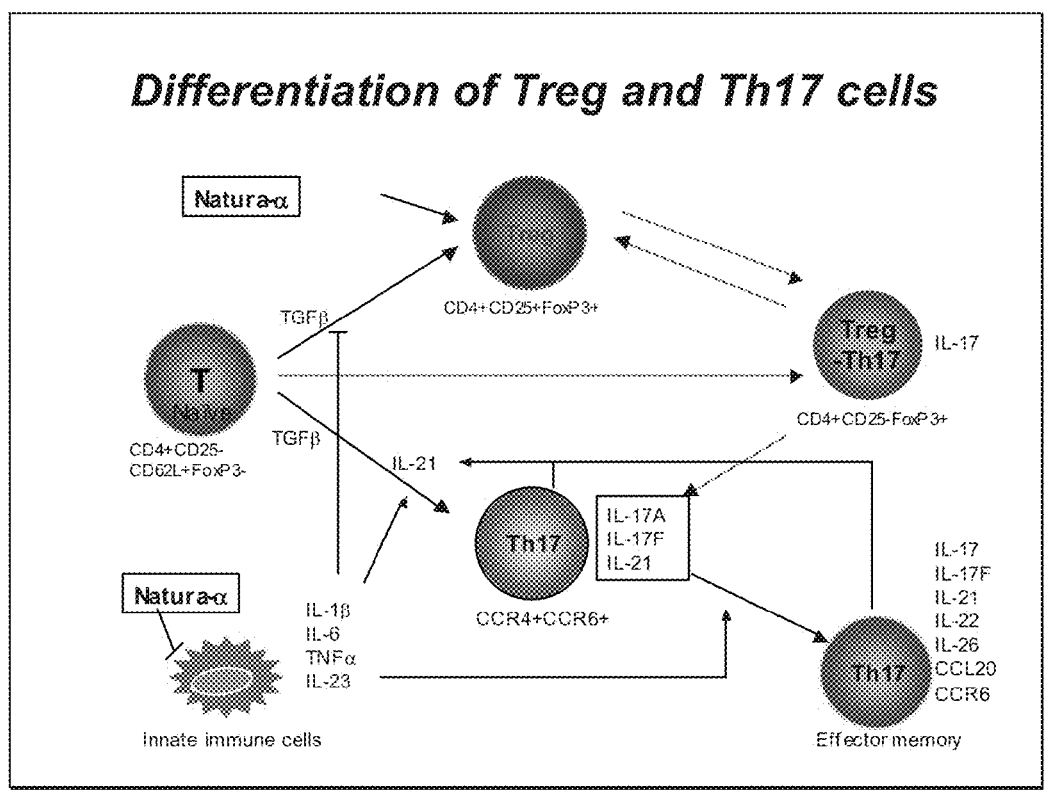
FIG. 1 is a schematic representation of mechanisms of Meisoindigo in treating autoimmune disease: Th17 cells are a major driving force of lupus through pro-inflammatory cytokines such as IL-17A, IL-17F and IL-21 as well as others. Under normal physiological conditions, activity of Th17 cells is well balanced by the activity of anti-inflammatory Treg cells. Autoimmune diseases will occur when the balance is skewed. Meisoindigo (Natura-$\alpha$) inhibits proliferation/differentiation of Th17 through repression of inflammatory cytokines such as, IL-$\beta$, IL-6, TNF-$\alpha$ in innate immune cells, such as monocytes; while promoting differentiation of Tregs and shifting a Th1 response to a Th2 response.

All patents and literature references cited in this specification are hereby incorporated by reference in their entirety.

The present invention is directed to pharmaceutical compositions and methods of treating lupus. The method preferably includes the step of administering to an animal a therapeutically effective amount of at least one compound selected from the group consisting of: indigo, isoindigo, indirubin or derivatives thereof.

Lupus is a chronic and prototypical systemic autoimmune disease characterized by multisystem microvascular inflammation leading to organ damage as a result of loss of tolerance to self-antigens. Lupus, includes systemic lupus erythematosus, which is the most common and serious form of lupus. Symptoms of lupus can occur in any part of the body, including the skin, heart, lungs, kidneys, joints and/or nervous system.

The therapeutically "effective amount" is the amount necessary to treat the lupus and/or a symptom of lupus. The effective amount can be determined, in accordance with the invention, by administering to a plurality of tested subjects various amounts of the active agent and then plotting the physiological response (for example an integrated "lupus index" combining several of the therapeutically beneficial effects) as a function of the amount. The amount above which the therapeutic beneficial effects begin to decrease (but is still lower than the maximum tolerable dose (MTD)) is the "effective amount." Due to statistical distribution typically the "effective amount" is not a single parameter but a range of parameters.

The terms "treating" or "treatment" in the context of the present invention refer to any improvement in the clinical symptoms of the lupus, as well as any improvement in the well-being of the patients, in particular an improvement manifested by at least one of the following: decreased joint pain, swelling and redness, low grade fever, skin rashes, vasculitis, fatigue, loss of appetite, nausea, and weight loss, chest pain, bruising, menstrual irregularities, sleep disorders, such as restless legs syndrome and sleep apnea, dryness of the eyes and mouth, brittle hair or hair loss, increase in the remission period between acute disease attacks; decrease in the time length of the acute attack; prevention of the onset of severe disease, etc. The treatment may also include: improvement in renal functions (decrease in blood urea, creatinine, or proteinuria). It should be understood that the present methods include, but are not limited to, treating lupus by preventing inflammation associated with the disease. In one embodiment, this is accomplished by administering an amount sufficient to regulate the cytokines and Th1, Th17, and Treg cell functions involved in the pathological progress of the lupus.

In a preferable embodiment, the invention is directed to the treatment of an animal diagnosed as having lupus or susceptible thereto. Preferably, the animal is a mammal (e.g., a horse, cow, dog, cat, sheep, etc.) and more preferably, the animal is a human. For administration to non-human animals in particular, the composition containing the therapeutic compound may be added to the animal's feed or drinking water. In addition, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

It should be understood that the present method includes, but is not limited to, treating lupus by reducing inflammation associated with the disease through modulation of cytokines involved in the pathological progress. When the method is directed to an animal susceptible to lupus, the method includes, but is not limited to, inhibiting the onset of the disease. Accordingly, in yet another preferred embodiment, the compound being administered is in an amount sufficient to treat lupus by inhibiting pro-inflammatory cytokine expression and/or by stimulating anti-inflammatory cytokines, but less than sufficient to substantially inhibit cyclin dependent kinases (CDKs).

As used herein, "to substantially inhibit CDKs" means a concentration sufficient to inhibit 30%, more preferably 40% or 45%, and most preferably a concentration equal to or higher than the inhibitory concentration 50% ($IC_{50}$) for CDKs. The CDK that is inhibited is preferably one or more CDK selected from the group consisting of CDK1, CDK2, CDK4 CDK5, and CDK6.

Preferably, the compound is administered in an amount sufficient to inhibit pro-inflammatory cytokine expression and/or to stimulate anti-inflammatory cytokine expression. In one embodiment, the compound is preferably administered in an amount sufficient to inhibit at one or more of the pro-inflammatory cytokines selected from the group consisting of: IL-1$\alpha$, $\beta$, IL-2, IL-3, IL-6, IL-7, IL-9, IL-12, IL-17, IL-18, TNF-$\alpha$, LT, LIF, Oncostatin, and IFNc1$\alpha$, $\beta$, $\gamma$ by at least 10% and more preferably 30%. In another embodiment, the compound is preferably in an amount to stimulate anti-inflammatory cytokine expression. In this embodiment, the compound is preferably administered in an amount sufficient to increase the anti-inflammatory cytokine selected from the group consisting of: cytokine IL-4, IL-10, IL-11, W-13 or TGF$\beta$ by at least 25%, more preferably at least 50%, and most preferably at least 75%. In a most preferable embodiment, the compound is administered in an amount sufficient to modulate cytokines TNF-$\alpha$, IL-1$\beta$, IL-6, IL17, and IL-10.

The compound is preferably administered in an amount sufficient to reduce proteinuria concentration by at least 30%. Accordingly, the method may also be used in the treatment of nephritis. Preferably, the nephritis is glomerulonephritis.

In one non-limiting embodiment, the compound is administered in an amount sufficient to modulate a humoral response in the animal being treated, preferably resulting in a decrease in total IgG antibodies within the animal. Preferably, total IgG antibodies are decreased by at least 10%, and more preferably by at least 30%.

It should also be noted that therapeutic benefits are typically realized by the administration of at least 1, 2, 3 or more of the compounds concurrently or sequentially. The compounds of the invention may also be combined with other therapies to provide combined therapeutically effective amounts. The compound can be administered, for example, in combination or in conjunction with additional agents, preferably anti-inflammatory agents, or corticosteroid, or immunosuppressant, such as methotrixate; or 4) a biologic disease modifying drug, such as belimumab (Benlysta®). For example, in one embodiment the anti-inflammatory agent is administered separately by injection and the compound of the invention is concurrently or sequentially administered orally and/or topically.

Chemical Structures:

The present invention is directed to a specific group of compounds that include isoindigo, indigo, indirubin and derivatives thereof. Preferably, the compounds are Meisoindigo, tri-acetylated glyco-Meisoindigo (pro-drug) and NATURA, shown as Formulas (IV), (V), and (VI) respectively.

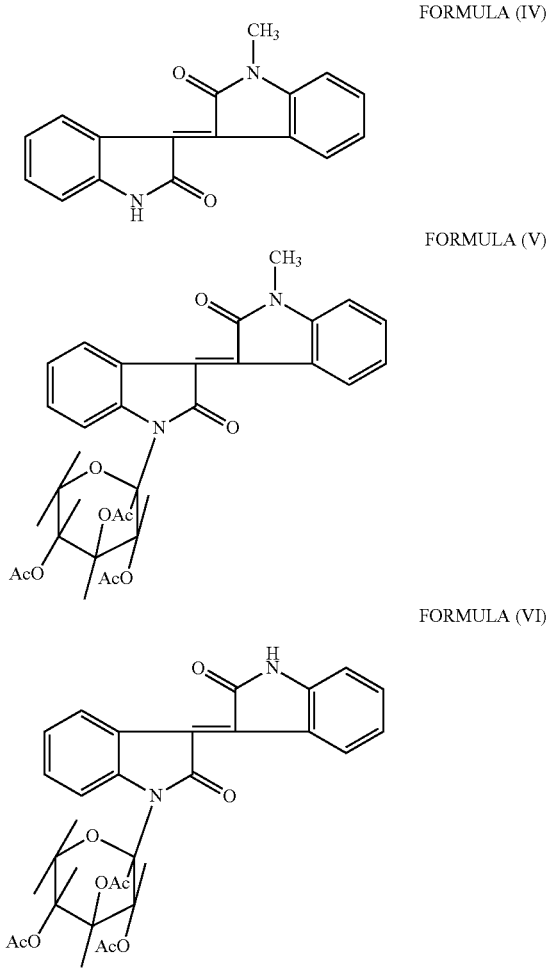

FORMULA (IV)

FORMULA (V)

FORMULA (VI)

The examples given below are simply to demonstrate different embodiments of the invention and are not intended in any way to limit the scope of the present invention thereto.

Compositions and Dosage Forms:

In a preferred embodiment, the compound is incorporated in a pharmaceutical composition that includes a pharmaceutically acceptable carrier. Advantageously, the composition may further include one or more anti-lupus agents. The anti-lupus agent can be any agent useful in treating lupus. Preferably the anti-lupus agent can be an anti-inflammatory agent, a corticosteroid, an immunosuppressant or a biologic antibody drug. In an alternative embodiment, the anti-inflammatory arthritis agent is separate. Examples of preferred anti-inflammatory agent include acetaminophen, aspirin, codeine, propoxyphene, fentanyl, palladone, morphine, morphine sulfate, oxycontin, aspirin, pentazocine, tramadol, hydrocodon, naproxen, indomethacin, ibuprofen, fenoprofen, ketorolac tromethamine, choline magnesium trisalicylate, rofecoxib, and combinations thereof.

Examples of preferred COX-2 inhibitors include rofecoxib, parecoxib, etoricoxib, and celecoxib.

Examples of preferred corticosteroids include betamethasone, cortisone, dexamethasone, hydrocortisone, methylprednisolone, prednisolone, prednisone, triamcinolone, and combinations thereof.

Examples of preferred NSAIDs include salicylate, arylalkanoic acid, 2-arylpropionic acid, N-arylanthranilic acid, oxiam, coxib, and sulphonanilide.

Examples of preferred immunosuppressants and biologics include hydroxychloroquine, chloroquine, leflunomide, methotrexate, sulfasalazine, gold, gold thiomalate, aurothioglucose, auranofin, azathioprine, cyclophosphamide, anti-tumor necrosis factor (anti-TNF, e.g., etanercept, infliximab, and adalimumab), anti-IL-1, Anti-CD20, anakinra, belimumab (Benlysta®), or combinations thereof.

In another preferred embodiment, pharmaceutical composition comprises Meisoindigo (NATURA-α) and/or NATURA. Typically the pharmaceutically acceptable carrier is an inert diluent.

The pharmaceutical compositions of the invention can take a variety of forms adapted to the chosen route of administration as discussed above. Those skilled in the art will recognize various synthetic methodologies that may be employed to prepare non-toxic pharmaceutically acceptable compositions of the compounds described herein. Those skilled in the art will also recognize a wide variety of non-toxic pharmaceutically acceptable solvents that may be used to prepare solvates of the compounds of the invention, such as water, ethanol, mineral oil, vegetable oil, and dimethylsulfoxide.

Pharmaceutical compositions can be used in the preparation of individual dosage forms. Consequently, pharmaceutical compositions and dosage forms of the invention comprise the active ingredients disclosed herein. The notation of "the compound" signifies the compounds of the invention described herein or salts thereof. Pharmaceutical compositions and dosage forms of the invention can further comprise a pharmaceutically acceptable carrier.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which an active ingredient is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, other excipients can be used.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral, topical, or mucosal administration to a patient, including suspensions (e.g., aqueous or non-aqueous liquid suspensions, oil-in-water emulsions, or a water-in-oil liquid emulsions); solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their route of administration and animal being treated. For example, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water.

The invention further encompasses pharmaceutical compositions and dosage forms that comprise one or more compounds that reduce the rate by which an active ingredient will decompose. Such compounds, which are referred to herein as "stabilizers" include, but are not limited to, antioxidants such as ascorbic acid, pH buffers, or salt buffers.

Furthermore, in yet another embodiment the compound—isoindigo, indigo, indirubin, or a derivative thereof—is in an amount sufficient to treat the inflammatory-related disease by inhibiting pro-inflammatory cytokine expression and/or by stimulating anti-inflammatory cytokine expression, but less than sufficient to substantially inhibit cyclin dependent kinases. In this embodiment, the additional anti-inflammatory agent mentioned above is not required in the composition to be effective, but is advantageous.

In one preferred embodiment, the dosage amount of the activate is less than sufficient to inhibit 50%, 40%, 30%, or 20% of cyclin dependent kinases selected from the group consisting of: CDK2, CDK4, and CDK6. Cell cycle progression and cell division are driven by the sequential activation of a group of CDKs (e.g., CDK2, CDK4, and CDK6). Despite this sequential activation, a high level of functional redundancy exists among these CDKs. As a result, the Mitotic Index (MI) was developed as a standard measure of the proliferation status of a cell population. It is defined as the ratio between the number of cells in mitosis and the total number of cells. This index is used to study the activity of CDK inhibitors and/or cell proliferation [6-7]. The mitotic index can be measured under light microscopy from a slide. To calculate the MI, one divides the number of cells containing visible chromosomes by the total number of cells in the field of view. Another important biomarker widely used to measure cell proliferation is ki67 [6, 8]. The ki-67 protein is present during all active phases of the cell cycle but is absent from resting cells, making it an excellent marker for determining the growth fraction of a given cell population. Thus, cells in the cell cycle can be identified using antibodies against the nuclear antigen ki-67, which, as explained above, is strictly associated with cell proliferation. Inhibition of proliferation can therefore be directly correlated to CDK inhibition by one skilled in the art.

For a particular condition or method of treatment, the dosage is determined empirically, using known methods, and will depend upon facts such as the biological activity of the particular compound employed, the means of administrations, the age, health and body weight of the host; the nature and extent of the symptoms; the frequency of treatment; the administration of other therapies and the effect desired.

The dosage is generally from 0.036 µmol/kg/day to 543.4 µmol/kg/day (i.e. in case of Meisoindigo, the dose range is 0.01 mg/kg/day to 150 mg/kg/day) and more preferably 18.1 µmol/kg/day to 362.3 µmol/kg/day (i.e. in case of Meisoindigo, the dose is 5-100 mg/kg/day). In one particular embodiment, the animal is a human and the amount is from 18.1 µmol/day to 362.3 µmol/day (i.e. when use Meisoindigo, the dose is 5-100 mg/day). Dosage unit forms will generally contain between from about 1 mg to about 100 mg of the compound.

For illustrative purposes, dosage levels of the administered active ingredients in animals may be: intravenous, 0.036 to 7.24 µmol/kg (i.e. if Meisoindigo is used, the dose will be equal to 0.01 to about 2 mg/kg); intramuscular, 0.181 to 18.12 µmol/kg (i.e. if Meisoindigo is used, the dose will be equal to 0.05 to about 5 mg/kg); orally, 0.181 µmol/kg to 362.3 µmol/kg (i.e. if Meisoindigo is used, the dose will be equal to 0.05 to about 100 mg/kg); intranasal instillation, 1.812 µmol/kg to 36.23 µmol/kg (i.e. if Meisoindigo is used, the dose will be equal to 0.5 to about 10 mg/kg); and aerosol, 1.81 µmol/kg to 362.3 µmol/kg (i.e. if Meisoindigo is used, the dose will be equal to 0.5 to about 100 mg/kg of host body weight). The dose level is usually about 10 times less in human than other animals. The various possible dosages and methods of administration are given as illustrative examples only. The actual dosages and method of administration or delivery may be determined by one of skill in the art.

Frequency of dosage may also vary depending on the compound used and whether an extended release formulation is used. For treatment of most disorders, however, a dosage regimen of three times daily or less is preferred. In a preferred embodiment, the treatment scheme is twice a day or less.

Preferably the compound is administered to the animal for a period of at least one week, more preferably for at least 3 months, and even more preferably for at least 6 months. Applicants have discovered benefits of continuous extended administration of the compound to the animal being treated. In certain embodiments, administration may be for at least 9 month, at least a year or even longer. For certain lupus conditions, the treatment may require continuous administration during the life of the animal being treated.

Expressed in terms of concentration, a compound may be present in the compositions of the present invention for localized use about the cutis, intranasally, pharyngolaryngeally, bronchially, intravaginally, rectally, or ocularly in concentration of from about 0.01 to about 30% w/w of the composition; preferably about 1 to about 20% w/w of the composition; and for parenteral use in a concentration of from about 0.05 to about 10% w/v of the composition and preferably from about 0.1 to about 10% w/v.

Preferred compounds of the invention to be used in the compositions will have desirable pharmacological properties that include, but are not limited to, oral bioavailability, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, Natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an active ingredient, anhydrous lactose, microcrystalline cellulose, polyvinylpyrrolidone, stearic acid, colloidal anhydrous silica, and gelatin.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous, bolus injection, intramuscular, and intra-arterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan mono stearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts of the active ingredients can be used to further adjust the properties of the resulting composition.

It is to be understood that the foregoing describes preferred embodiments of the present invention and that modifications may be made therein without departing from the spirit or scope of the present invention as set forth in the claims.

The present invention will now be illustrated by the following non-limiting examples. It is to be understood that the foregoing describes preferred embodiments of the present invention and that modifications may be made therein without departing from the spirit or scope of the present invention as set forth in the claims.

EXAMPLES

Example 1

Meisoindigo Reduces the Secretion of IL-β in Human Monocytic Cell Line THP-1 Cells

Materials and Methods

Materials:

Meisoindigo and NATURA were synthesized by Natrogen Therapeutics, Inc, purified by high performance liquid chromatography (HPLC) with a purity of 98.5%, and their structures confirmed by mass spectrometry and nuclear magnetic resonance (NMR). Meisoindigo is a dark-reddish crystal, with a molecular weight of 376. It was prepared in a solution of dimethyl sulfoxide (DMSO), and stored under −20° C. for the experiments in vitro. Human monocytic cell line, THP-1 (90), was purchased from ATCC. The cells were maintained according to the supplier's instructions. Approximately $1\times10^5$ cells/ml were cultured at 37° C., 5% $CO_2$ for 24 hours in Modified RPMI-1640 Medium (Invitrogen) supplemented with 10% FBS.

Figure 2:
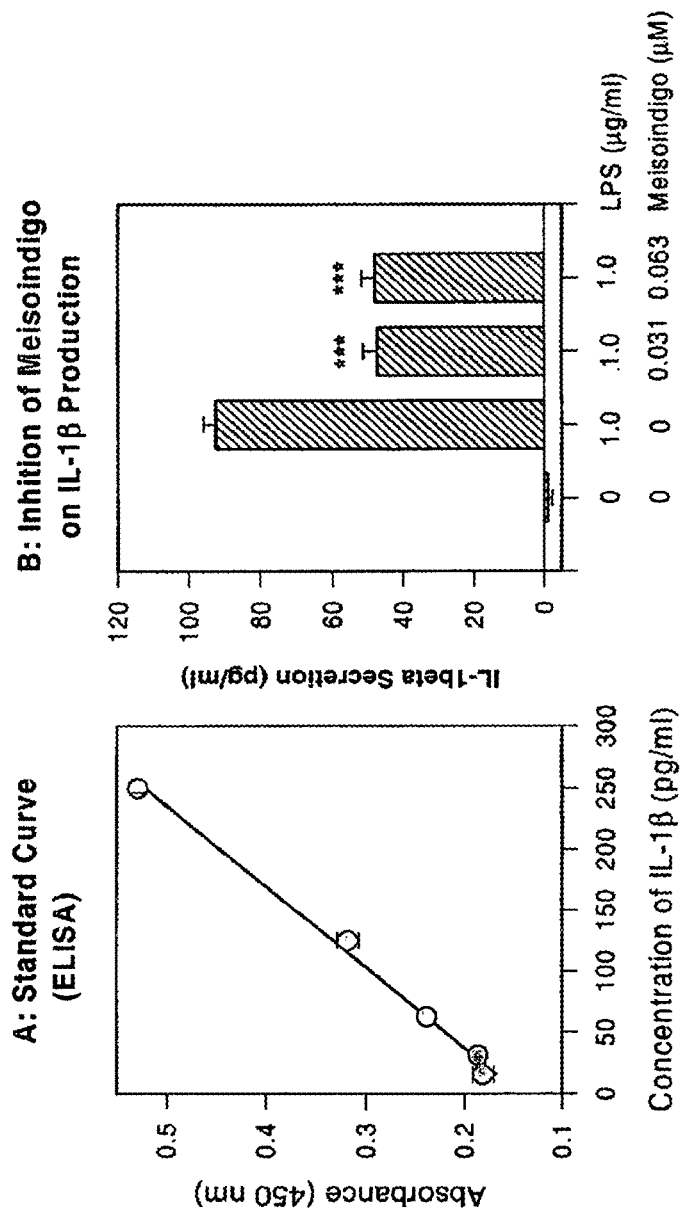
FIG. 2 shows the effect of Meisoindigo on the secretion of IL-1β in LPS stimulated human monocytic THP-1 cells. Inhibitory effect of Meisoindigo on IL-1β production in LPS-stimulated human monocytic THP-1 cells. The THP-1 cells were treated/stimulated with and without 1 µg of lipopolysaccharide (LPS, Sigma), and exposed for 24 hrs to a series of concentrations of Meisoindigo (from 31.25 nM to 16,000 nM). Viability of cells was examined under the microscope after trypan blue staining. Protein levels of IL-1β secreted into the culture media were measured by ELISA and calculated from its standard curve (panel A) using an assay Kit from R&D Systems as described in Materials and Methods in Example 1 below. The student t-test was used to determine the statistically significance, *** indicates P<0.001. As shown in panel B, Meisoindigo significantly inhibits IL-1β production at concentration as low as 31 nM.

Methods:

The cells were stimulated with or without 1 μM of lipopolysaccharide (LPS, Sigma), and exposed for 24 hours to different concentrations of Meisoindigo (from 31.25 nM to 16,000 nM). Viability of cells was examined under microscope after trypan blue staining. Protein levels of IL-1β secreted into the culture media by the cells were then measured by ELISA and calculated from its standard curve using an assay Kit from R&D Systems according to instructions provided by the supplier. The method was established and validated by a good standard curve obtained. An example of the standard curve is shown in FIG. 2, panel A.

Statistical Analysis:

All data were expressed as a mean±SD. Statistical significance of any difference between the control (LPS) and experimental groups was determined by the Student's t-test. P values between the 2 groups must be at least smaller than 0.05 to be considered statistically significant.

Results and Discussion

IL-1β is a pleiotropic pro-inflammatory cytokine involved in the pathological process of various inflammatory-related diseases. To elucidate the activity of Meisoindigo, a representational small molecule of derivatives of indigo, isoindigo and indirubin, against inflammation, we examined the activity of Meisoindigo on the secretion of IL-1β in human monocytic THP-1 cells. As shown in FIG. 2, panel B, the basal level of IL-1β in human monocytic THP-1 cells was found to be undetectable. It has been demonstrated previously that increases of protein IL-1β and mRNA levels in response to lipopolysaccharide (LPS), predominantly are a result of increased transcription of the gene [9-10]. In this invention, we also observed that upon stimulation of LPS, the THP-1 cells secreted a large amount of IL-1β into the medium (92.38±3.667 pg/ml, FIG. 2, panel B). Interestingly, the stimulated secretion of IL-β was significantly inhibited by simultaneously exposing the cells to Meisoindigo. Most importantly, we found that Meisoindigo was a potent, but also moderate IL-1β inhibitor.

This characteristic will be an advantage to patients for high efficacy with lesser side effects when it is used for the treatment of inflammatory disorders. Potent, because over 50% reduction of the LPS mediated IL-1β secretion was repeatedly achieved when the cells were exposed to Meisoindigo at concentrations as low as 31.25 nM; moderate, because increasing the concentration of Meisoindigo up to 8 μM did not result in further reduction of the secretion, indicating that the activity reached was maximal. This is different from the effect of Meisoindigo or NATURA on the inhibition of cyclin-dependent kinases (CDKs) in which a much higher concentration is needed for the 50% inhibition of CDK activity (approximately 1.6 μM) in LNCaP prostate cancer cells as demonstrated in our previous patent.

The last point is significant since the prior art EP 1 079 826 only set out to inhibit CDKs, rather than cytokines. As a result, much lower concentrations of medicaments are employed in the present invention as compared to the prior art. Furthermore, particular derivatives may also be more suitable for cytokine inhibition as compared to CDK inhibition.

Example 2

Meisoindigo Inhibits the Secretion and Expression of IL-6 in Human Monocytic Cell Line THP-1 Cells

Materials and Methods

Figure 3:
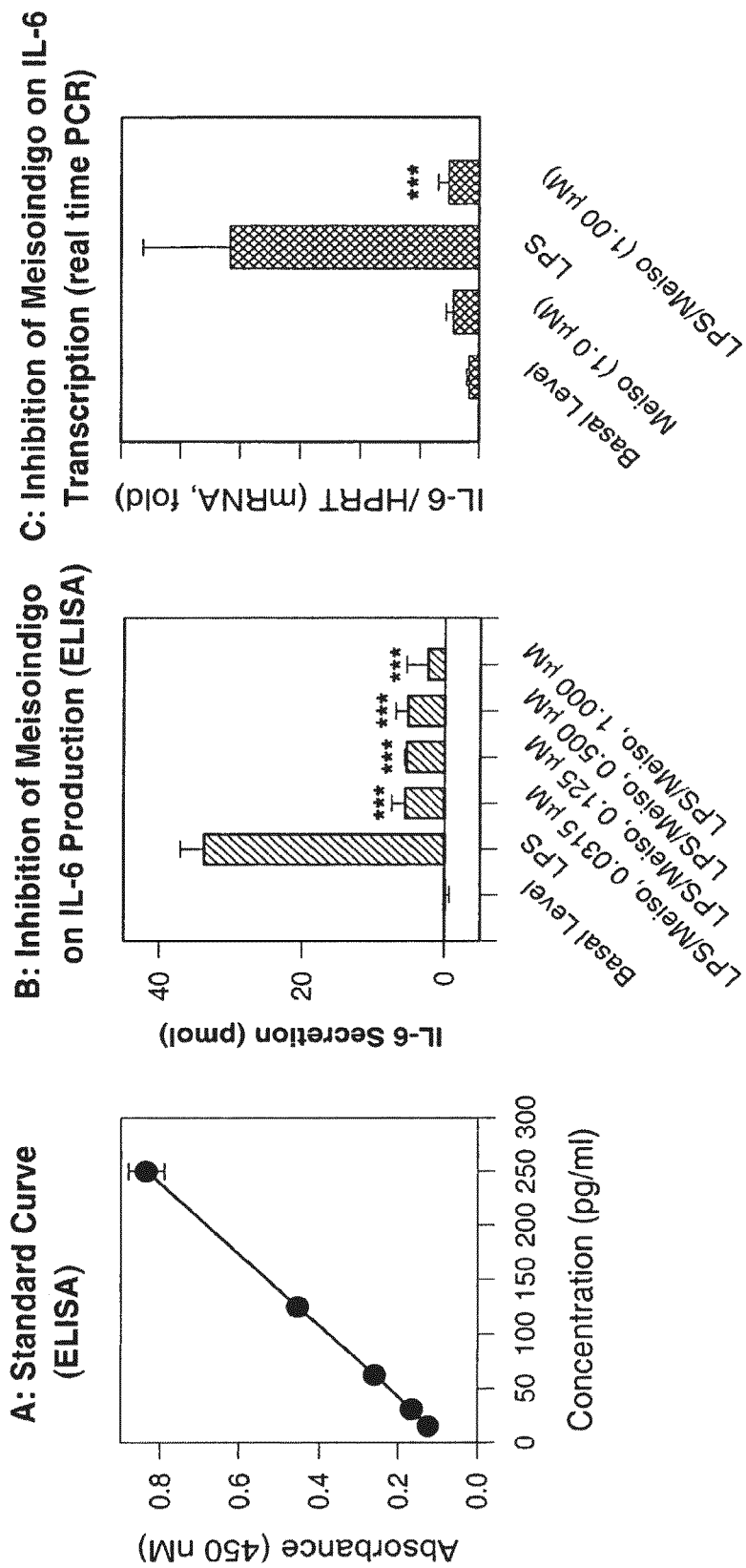
FIG. 3 shows the effect of Meisoindigo on the secretion and expression of IL-6 in LPS stimulated human monocytic THP-1 cells. Effects of Meisoindigo on the production (panel B) and transcription (panel C) of IL-6 in LPS-stimulated THP-1 cells: THP-1 cells were treated/stimulated with and without 1.0 µg/ml of LPS and exposed to a series of concentrations of Meisoindigo (from 0.031 to 16 µM) for 24 hrs. The IL-6 protein in the media was measured by ELISA, and the IL-6 transcription in cells was measured by real time PCR as described in Materials and Methods in Example 2 below. Panel A: Standard curve established using the pure IL-6 protein and used for the calculation of the protein production in panel B; Panel C: real time PCR assay for the transcription of IL-6. ***: P<0.001. As shown in panel B and C, Meisoindigo significantly inhibits both secretion and transcription of IL-6.

Materials:

The representative derivative Meisoindigo was used. The cell line and the procedure of ELISA were the same as described in Example 1. Standard IL-6 protein was used to establish a standard curve for the calculation of IL-6 in the medium secreted by the cells (LPS-stimulated or non-stimulated cells in the presence or absence of Meisoindigo). A typical standard curve is shown in FIG. 3, panel A. Statistical analysis also followed the method described in Example 1.

Methods:

Real Time PCR:

The effect of Meisoindigo on the transcription of IL-6 (RNA levels) was determined by a technique of real time polymerase chain reaction (real time PCR). Total RNA was extracted using a Qiagen Rneasy minit kit, and the HPRT gene was used as internal control.

Human monocytic THP-1 cells at exponential growth phase were exposed to 1 μg/ml of LPS, 1 μM of Meisoindigo, or 1 μg/ml of LPS plus 1 M of Meisoindigo for 24 hours. The cells were then harvested, washed and total RNA extracted for real time PCR assay. Total RNA (300 ng) was treated with DNase I (Promega, Madison, Wis.), and SuperScript II (Invitrogen, Carlsbad, Calif.) and oligo(dT) were used for reverse transcription according to the manufacturers' instructions. Real-time PCR reactions were performed in a 25-μL volume containing diluted cDNA, Sybr Green PCR Master Mix (Applied Biosystems), and 2.5 μM each IL-6 gene-specific primer: R: 5'-TCAATTCGTTCTGAAGAGG (SEQ ID NO. 1) and F: 5'-CCCCCAGGAGAAGATTCC (SEQ ID NO. 2). An ABI SDS7700 analyzer (Applied Biosystems) was used at 50° C. for 2 minutes and 95° C. for 10 minutes, followed by 40 cycles at 95° C. for 15 seconds and 60° C. for 1 minute. Test cDNA results were normalized to HPRT internal control measured on the same plate. After cycling, the specificity of amplification was validated by the generation of a melting curve through slow deNaturation of the PCR products and then by gel electrophoresis.

Results and Discussion

IL-6 is another key pro-inflammatory cytokine involved in inflammation. Therefore, the effect of Meisoindigo on the secretion/expression was examined. Similar to IL-1β, the basal level of IL-6 was undetectable in human monocytic THP-1 Cells. Upon stimulation with 1 μg/ml LPS, the cells moderately secreted IL-6 into the media (33.64±3.29 pg/ml). Meisoindigo was found to strongly inhibit the secretion of IL-6 in the LPS stimulated THP-1 cells. Approximately 85% of the reduction of secretion was observed when the stimulated cells were exposed to Meisoindigo at the lowest concentration of 31.25 nM of the experiment (P<0.001) (FIG. 3, panel B).

To explore whether the reduction of IL-6 secretion mediated by Meisoindigo was due to its inhibition on the LPS stimulated expression of IL-6, a real time PCR was applied to measure the effect of Meisoindigo on the IL-6 mRNA transcription. As shown in FIG. 3, panel C, a significant induction of IL-6 transcription was observed when the THP-1 cells were exposed to 1 μg/ml LPS, which is consistent with the previous reports (93). Interestingly, the LPS-induced IL-6 transcription could be completely suppressed by exposing the LPS-stimulated THP-1 cells to 1 μM of Meisoindigo (P<0.001). This finding thus indicates that the inhibition of Meisoindigo on LPS-stimulated secretion of IL-6 probably results from the suppression of the agent on LPS-mediated IL-6 production in THP-1 cells.

Stimulation of LPS on human monocytes activates IL-6 transcriptional signaling pathways. LPS can bind to a protein termed a LPS binding protein (LBP). It has been shown that after its transfer by LBP to the CD14 receptor, LPS interacted with the signaling receptor TLR4 and the accessory protein MD-2. This interaction resulted in the activation of NF-κB and 3 MAP kinases, thus increasing IL-6 transcription [11-12]. Whether suppression of Meisoindigo on LPS-mediated IL-6 transcription is due to the interruption of the signal transduction pathways needs to be further investigated.

Example 3

Meisoindigo Suppresses the Secretion of TNF-α in Human Monocytic THP-1 Cells

Materials and Methods

Figure 4:
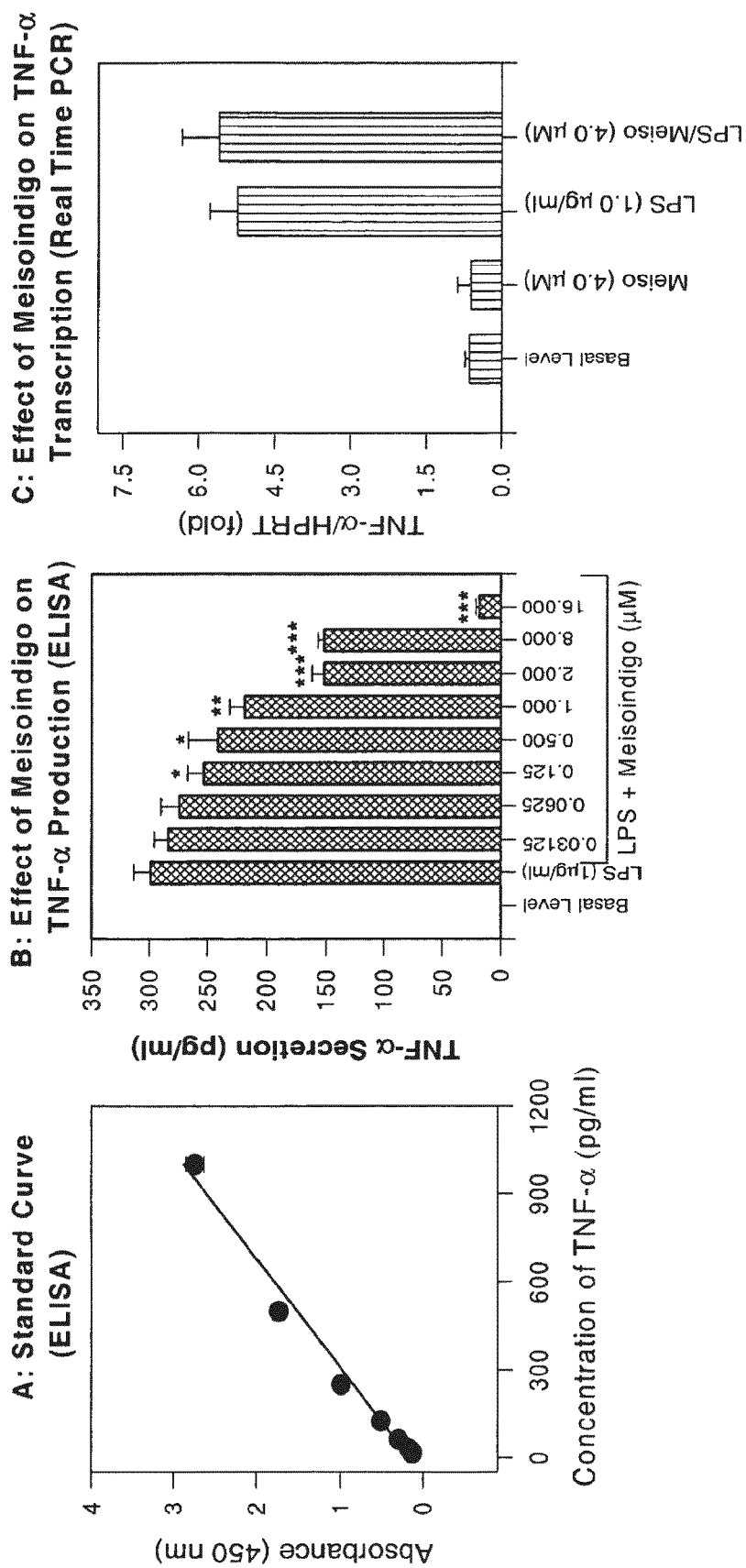
FIG. 4 shows the effect of Meisoindigo on TNF-α secretion and expression in human monocytic THP-1 cells. Effects of Meisoindigo on the protein production (panel B) and gene transcription (panel C) of TNF-α in LPS-stimulated THP-1 cells: THP-1 cells were treated/stimulated with and without 1.0 µg/ml of LPS and exposed to a series of concentrations of Meisoindigo (from 0.031 to 16 µM) for 24 hrs. The TNF-α protein in the media was measured by ELISA, and its transcription in cells was measured by real time PCR technology as described in Materials and Methods in Example 3 below. Panel A: Standard curve established using the pure TNF-α protein and used for the calculation of the protein production in panel B. A concentration-dependent inhibition of Meisoindigo on TNF-α secretion was obtained (panel B). Panel C: real time PCR assay for the transcription of TNF-α. No effect of the agent on TNF-α transcription was observed. ***: P<0.001.

The representative derivative Meisoindigo was used. The cell line and the procedure of ELISA to measure secretion of TNF-α were the same as described in Example 1, except the standard TNF-α protein was used to establish a standard curve for the calculation of the protein secreted in the medium by the cells (LPS-stimulated or non-stimulated cells in the presence or absence of Meisoindigo). A typical standard curve is shown in FIG. 4, panel A.

The effect of Meisoindigo on the transcription of TNF-α (RNA levels) was determined by a technique of real time PCR using the same procedures described in Example 2, except the specific primers for TNF-α were used as follows: 5'-TGC-CCAG-ACTCGGCAAAG (SEQ ID NO. 3), and 5'GGAGAAGGGTGACCGACT (SEQ ID NO. 4). Total RNA was extracted using a Qiagen Rneasy minit kit, and the HPRT gene was used as internal control.

Human monocytic THP-1 cells grown exponentially were exposed to 0.1 μg/ml of LPS, 4 μM of Meisoindigo, or 1 μg/ml of LPS plus 4 μM of Meisoindigo for 24 hours. The cells were then harvested, washed and total RNA extracted for real time PCR assay as described in Example 2.

Results and Discussion

TNF-α is a crucial pro-inflammatory cytokine investigated extensively during the past decade due to its important biological functions against cancer and its pathological role in the inflammatory disorders. Several inhibitors of TNF-α have been marketed for the treatment of various inflammatory-related diseases. As a potential anti-inflammatory agent, we explored a role of Meisoindigo in the regulation of TNF-α in this invention.

As an established model system, stimulation of THP-1 cells with LPS resulted in a huge secretion of TNF-α (FIG. 4, panel B). However, Meisoindigo effectively inhibited the secretion of TNF-α in the LPS-stimulated THP-1 cells in a concentration-dependent manner (FIG. 4, panel B). Approximately 50% reduction of the secretion was achieved when stimulated cells were exposed to 2.0 μM of Meisoindigo for 24 hours (P<0.001, as compared LPS plus Meisoindigo with LPS alone) at which no apoptotic cells were observed using trypan blue staining. Increasing the concentration of Meisoindigo up to 8 μM did not cause further reduction of TNF-α secretion while no cell deaths were observed. A complete inhibition was obtained however when the stimulated cells were treated with 16 μM of Meisoindigo at which approximately only 20% apoptotic cells appeared.

Real time PCR assays showed no effect of Meisoindigo (4 μM) on TNF-α mRNA levels (FIG. 4, panel C), indicating that reduction of TNF-α production in LPS-stimulated THP-1 cells by Meisoindigo occurs at post-transcriptional level. It is well established that AU-rich elements (ARE) in the TNF-α mRNA 3' UTR are involved in mRNA stability and translational efficiency [13]. TNF-α ARE is a target of the mRNA-stabilizing factor HuR [14]. Maturation of TNF-α, mRNA is affected by a cis-element (2-APRE) in the 3'UTR, which renders splicing of TNF-α precursor transcripts dependent on activation of RNA-activated protein kinase (PKR) [15].

Although the mechanisms by which Meisoindigo inhibits the secretion of TNF-α in LPS-stimulated THP-1 cells need to be established, Meisoindigo is a novel small molecule inhibiting TNF-α without cytotoxicities, which would make it an ideal medicine for the treatment of various inflammatory-related diseases.

Example 4

Meisoindigo Stimulates the Secretion of IL-10 in Human Monocytic THP-1 Cells

Materials and Methods

Meisoindigo and the THP-1 cell line used in this Example were the same as described in Example 1. The procedures of ELISA to measure the secretion of IL-10 also followed the procedures described in Example 1, except the standard IL-10 protein was used to establish the standard curve (FIG. 5, panel A) for the calculation of the protein secreted in the medium by the cells (LPS-stimulated or non-stimulated cells in the presence or absence of Meisoindigo).

Results and Discussion

Figure 5:
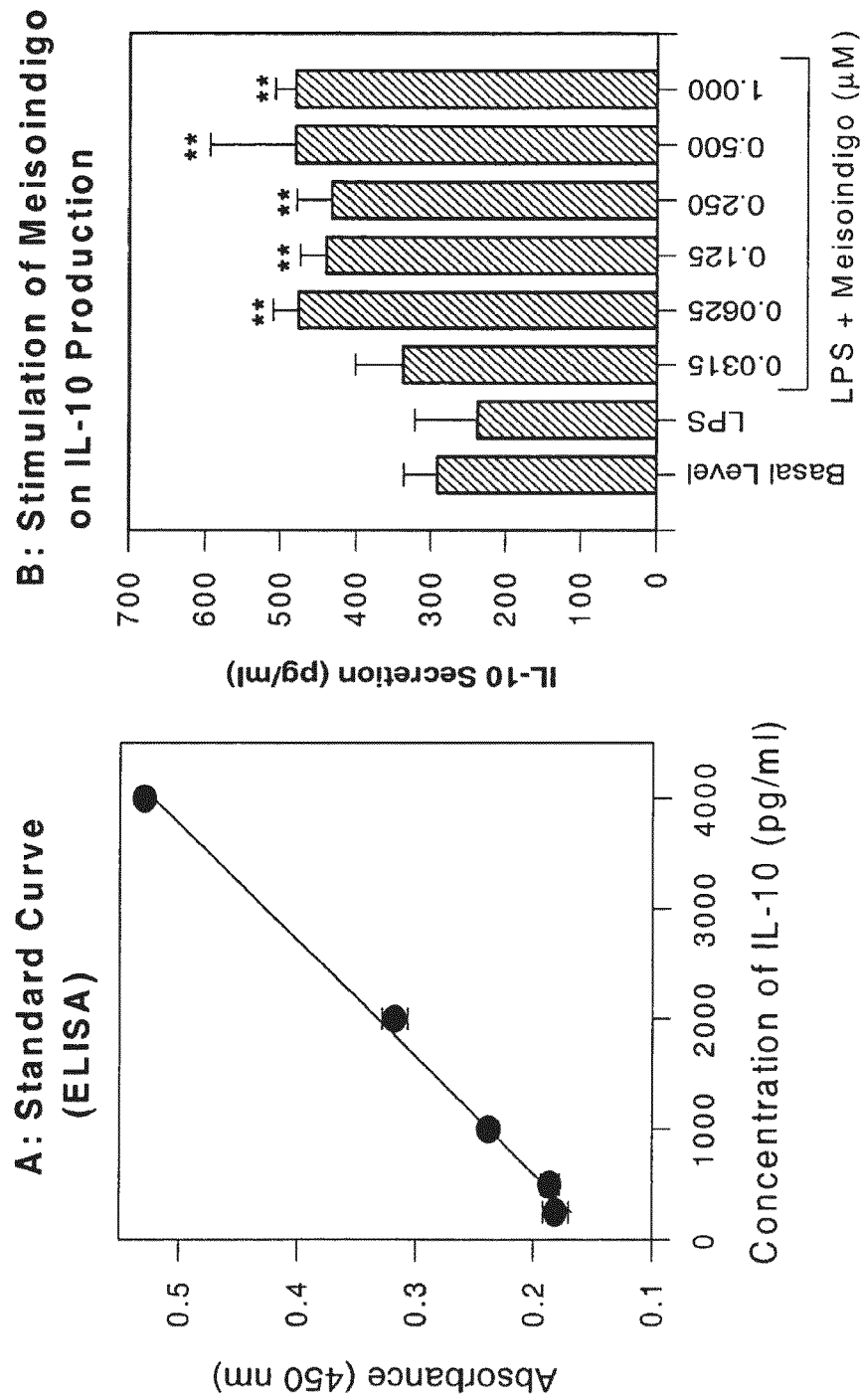
FIG. 5 shows stimulation of IL-10 by Meisoindigo in THP-1 cells. Stimulation of Meisoindigo on the production of IL-10 in LPS-treated THP-1 cells: THP-1 cells were treated with and without 1.0 µg/ml of LPS and exposed to a series of concentrations of Meisoindigo (from 0.031 to 16 µM) for 24 hrs. The IL-10 protein in the media was measured by ELISA as described in Materials and Methods in Example 4 below. Panel A: Standard curve established using the pure IL-10 protein and was used for the calculation of the protein production in panel B. While inflammatory stimulant LPS decreased the protein level of IL-10, Meisoindigo significantly increased the protein production, and the maximal stimulation effect occurred at 62.5 nM with approximately 2-fold increase of IL-10 secretion (panel B). **: P<0.01.

The functioning of the immune system is finely tuned by the activities of pro-inflammatory and regulatory mediators or cytokines, and inflammatory-related diseases have been considered a result of imbalance between these types of molecules [16-17]. To understand whether the anti-inflammatory effects of small molecules claimed in this invention are capable of induction of regulatory cytokines, the effect of Meisoindigo on the secretion of IL-10 was investigated. As shown in FIG. 5, panel B, a moderate but significant stimulation of IL-10 secretion in THP-1 cells was observed. Approximately 60% increase in the IL-10 secretion was achieved when the THP-1 cells were treated with 0.0625 μM of Meisoindigo (P<0.05). In contrast, as an inflammatory stimulator, LPS slightly decreased the secretion of cytokine.

Example 5

Meisoindigo and its Derivatives, at Low Concentrations, Select Cytokines Rather than CDKs as Primary Molecular Targets Materials and Methods Materials:

Meisoindigo and NATURA were synthesized by Natrogen Therapeutics, Inc, as described in the above examples.

Human monocytic cell line, THP-1 [18] was purchased from ATCC. The cells were maintained according to the supplier's instructions. Approximately $1\times10^5$ cells/ml were cultured at 37° C., 5% $CO_2$ for 24 hours in Modified RPMI-1640 Medium (Invitrogen) supplemented with 10% FBS.

Methods:
1) Effects of Meisoindigo and NATURA on the expression/secretion of cytokines IL-1β, IL-6, IL-10: The human monocytic THP-1 cells grown exponentially were stimulated with or without 1 μM of lipopolysaccharide (LPS, Sigma), and exposed for 24 hours to different concentrations of Meisoindigo and NATURA (from 31.25 nM and 62.5 nM), respectively. Viability of cells was examined by trypan blue exception assay. Protein levels of IL-1β secreted into the culture media by the cells were then measured by ELISA and calculated from its standard curve using an assay Kit from R&D Systems according to instructions provided by the supplier as described in the examples of 1 to 4.
2) Effects of Meisoindigo and/or NATURA on activity of cyclin dependent kinases (CDK) in THP-1 cells [19]: THP-1 cells grown exponentially were exposed to 31.25, 62.5, and 1500 nM of Meisoindigo or NATURA for 24 hr, respectively. The cells were harvested, washed, and total proteins extracted as described previously [20]. One hundred μg of the proteins were immuno-precipitated using antibodies against either cdk2, cdk4/6 or cyclin D1 overnight at 4° C. in the presence of a cocktail of protease inhibitors. The immuno-precipitates were washed 4 times with protein extraction buffer and once with kinase assay buffer, and reacted with 75 μg/ml histone H1 in the presence of $[\gamma\text{-}^{32}P]$-ATP (10 μCi/10 μM). The phosphorylated histone H1 (represent cdk activity) was measured by scintillation counting or by SDS-polyacrylamide gel electrophoresis [21-22].
3) Statistical Analysis: All data were expressed as a mean±SD. Statistical significance of any difference between the control (LPS) and experimental groups was determined by the Student's t-test. P values between the 2 groups must be at minimum smaller than 0.05 to be considered statistically significant.

Results and Discussion

Since it has been shown that indirubin and its derivatives inhibited cyclin dependent kinases, it thus could be an effective treatment of diseases associated with the loss of proliferation control via CDK inhibition. To examine which cellular molecules are primary targets related to the anti-inflammatory properties of this class of compounds, we compared how Meisoindigo and NATURA modulated n activities of CDKs and cytokines under the same experimental low concentration conditions.

Figure 6:
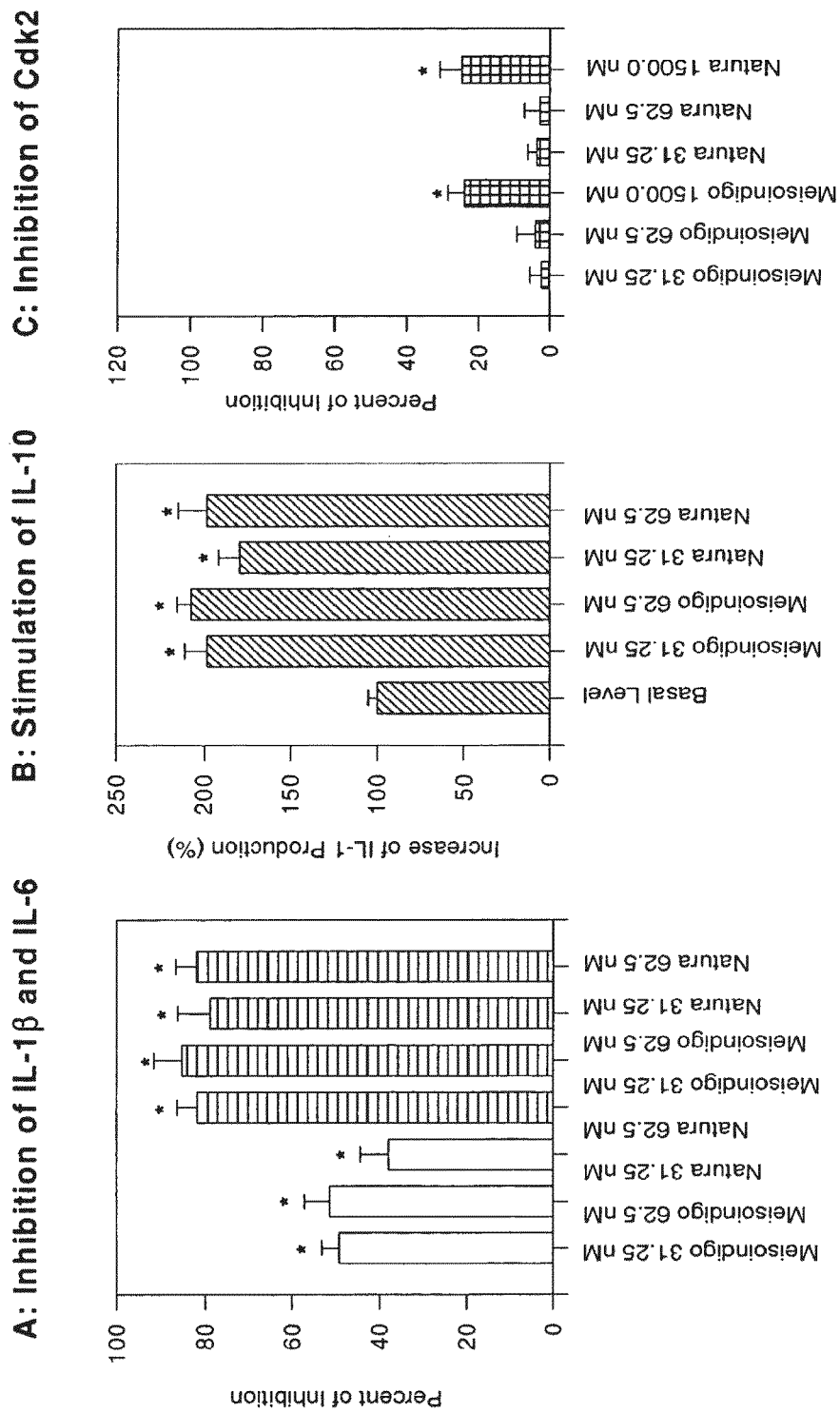
FIG. 6 shows the effects of Meisoindigo and NATURA on the Expression of Pro-inflammatory Cytokines and Cyclin-dependent Kinases in THP-1 cells: The THP-1 cells grown exponentially were stimulated with (panel A and B) and without (panel C) 1 µg LPS, and exposed for 24 hrs to the indicated concentrations of Meisoindigo or NATURA. Viability of cells was examined by trypan blue exception assay. Protein levels of IL-1β, IL-6 and IL-10 secreted into the culture media were measured by ELISA as described in the above examples using an assay Kit from R&D Systems as described in Materials and Methods of Example 5 below. The student t-test was used to determine the statistically significance, * indicates P<0.001. Meisoindigo and NATURA significantly inhibit production of IL-1β and IL-6, and promoted production of IL-10 at concentrations of 31.25 and 62.5 nM. In contrast, no inhibitory effect of the compounds on CDK2 was observed at the low concentrations (31.25 and 62.50 nM) under same experimental conditions.

As shown in FIG. 6, similar to the observation shown in the Examples 1, 2 and 4, LPS-stimulated increases of the production of IL-1β and IL-6 were significantly inhibited by exposure of the cells to both Meisoindigo and NATURA at as low as 31.25 nM, whereas LPS-mediated suppression of IL-10 in the THP-1 cells were elevated almost 2 fold by both Meisoindigo and NATURA under the similar concentrations (FIG. 6A).

In contrast, under the same exposures, both Meisoindigo and NATURA failed to inhibit activities of cyclin dependent 2, 4 and 6, as well as the levels of cyclin D1 (data not shown). A partial inhibition (23%) of those compounds was only achieved when the cells were treated with 1.5 μM (48-fold higher) of either Meisoindigo or NATURA (FIG. 6B).

In addition, the effect of NATURA on glycogen synthase kinase-3β (GSK-3β), was also investigated in the current invention, since CDK inhibitors usually are also inhibitors of GSK-3β. However, no activity was observed when the cells were exposed to NATURA at as high as 50 μM (data not shown).

Thus, the data in this example clearly shows that Meisoindigo and related class of molecules is able to significantly modulate various cytokines (inhibits pro-inflammatory cytokines, and stimulate anti-inflammatory cytokines) at remarkably low concentration; where no any inhibitory effects on CDK activity is achieved. This demonstrates that at low concentrations compared to those needed for CDK inhibition, that Meisoindigo and its derivatives primarily target, cytokines rather than cyclin dependent kinases. This conclusion is supported by the recently observation that Indirubin and its derivatives are not truly biological CDK inhibitors since the inhibition of CDK by those compounds are through physical aggregation rather than biological reaction [23]. Moreover our conclusion is also supported by the clinical observations that total dosage of 8696 mg of Meisoindigo is needed to achieved the maximal remission of chronic myeloid leukemia (CML) [24], whereas only 525 mg of the drug are needed to obtain a complete cure of the inflammatory bowel disease.

Summary

THP-1 cells secreted IL-1β, IL-6, IL-8 and TNF-α, but no IL-2, IL-4, IL-10 and IL-12 after 24 hours of the stimulation of LPS while the basal levels of these cytokines were undetectable by ELISA, which is consistent with the previous reports [25-26]. To evaluate the potential clinical applications of a class of small molecules of derivative of isoindigo, indigo, and indirubin (structures shown as Formulas I, II, and III) in the treatment of various inflammatory-related diseases, we examined the regulatory effects of Meisoindigo, as examples on the secretion and expression of pro- and anti-inflammatory cytokines in a human monocytic THP-1 cell model. The data is summarized in Table 2. Meisoindigo significantly inhibited secretions of pro-inflammatory cytokines IL-1β, IL-6, and TNF-α in LPS-stimulated THP-1 cells, and stimulated the secretion of regulatory cytokine IL-10, but no effects were observed on IL-2 simply because the cells were unable to be stimulated to secrete these pro-inflammatory cytokines. The maximal reductions or stimulations of the secretions of these cytokines are summarized in Table 1.

TABLE 1

Modulation of Meisoindigo on the secretion of pro-inflammatory and regulatory cytokines in LPS-stimulated THP-1 cells

| | Percentage of Maximal Response Without Cytotoxicity | | | |
|---|---|---|---|---|
| Treatment | TNF-α (Inhibition) | IL-1β (Inhibition) | IL-6 (Inhibition) | IL-10 (Stimulation) |
| LPS | 100.00 ± 4.85 | 100.00 ± 3.43 | 100.00 ± 9.78 | −18.27 ± 10.15 |
| LPS/Meisoindigo | 49.20 ± 3.37 | 48.76 ± 3.68 | 83.51 ± 5.41 | 201.97 ± 11.2 |

Reduction of IL-6 secretion by Meisoindigo in LPS stimulated THP-1 cells may be a result of the down-regulation of transcription of the cytokine gene by using a real time PCR technique. Real time PCR assay also showed a moderate inhibition of Meisoindigo on IL-15 in the LPS-stimulated THP-1 cells (data not shown). No such down-regulation was observed for TNF-α gene using the same technology. Although mechanisms by which Meisoindigo and molecules of this class regulate pro- and anti-inflammatory cytokines need to be further investigated, our data in the present invention demonstrates that this class of small molecules is capable of modulating important cytokines related to various inflammatory-related diseases.

During the past several years, strategies targeting pro-inflammatory cytokines have been created several protein-based agents for the treatment of various inflammatory disorders, including TNF-α inhibitors etaercept (ENBREL®), infliximan (REMICADE®; Centocor), adalimumab (HUMIRA®; Abbott) and IL-1 receptor antagonist KINERET®. Early stages of clinical application of these agents indicated that these revolutionary therapeutic agents have been an advancement in the treatment of autoimmune diseases such as IBD, RA, and psoriasis. However, the current injectable protein-based therapies have associated risks, including the potential for increased malignancies, infections and increased congestive heart failure [27]. Moreover, those strategies also have limitations and are challenged by the sophisticated cytokine network system. Although several types of small molecules have been shown to be a specific pro-inflammatory cytokine inhibitor, such as inhibitors of TNF-α and NF-κB, and have various advantages over the protein-based agents, targeting a single pro-inflammatory cytokine may not be strong enough to interrupt the inflammatory pathological pathways, and this limits their clinical efficacy.

In contrast, besides all the advantages of small molecules in clinical application, such as the fact that they are easy to make and convenient to administer, most importantly the molecules claimed in the invention not only concurrently suppress various pro-inflammatory cytokines, i.e., IL-1β, IL-6, and TNF-α, but also stimulate anti-inflammatory cytokine IL-10. Moreover these molecules have been demonstrated in our previous patent to induce cell differentiation and inhibit cell proliferation at higher concentration. Thus, they provide greater clinical activity. This conclusion has been supported by remarkable outcomes of the efficacy achieved using Meisoindigo for the treatment of a patient with IBD without any side effects.

Example 6

Meisoindigo and Natura Effectively Prevents and Treats Proteinuria in NZB/f1 Mice Animal models: There are at least four mouse models of lupus nephritis [28]. Both NZB×NZW F1 [29] and MRL/lpr mouse [30-31] strains spontaneously develop autoimmune lupus nephritis. Female mice from the NZB×NZW F1 cross (NZB/W) develop proteinuria and only a small number (<20%) survive to 52 weeks. In MLR/lpr mice, the disease develops in both males and females and is associated with the fas lpr mutation on the MLR background. Mice develop significant proteinuria at 16 weeks and show significant mortality rates (about 50%) by 20 weeks [32-33]. Among these models, both MLR/lpr and NZB/W mouse models have been widely used in drug development [34-36].

To determine whether Meisoindigo and Natura effectively prevents and treats proteinuria of lupus, NZB/W mice were used.

Materials:

Meisoindigo and Natura, were synthesized, purified and structure-characterized by the Natrogen Therapeutics, International, Inc. Suspension of Meisoindigo and Natura were prepared weekly in 0.5% tween 20 and stored at 4° C. The drug suspensions were given orally for purposes of the animal tests described below.

Animals:

NZB/W (New Zealand Black/New Zealand White, NZB× NZW F1 cross) female mice were purchased from the Jackson Laboratory (Bar Harbor, Me.). These mice were be maintained under pathogen-free barrier conditions, in accordance with guidelines from the American Association for the Accreditation of Laboratory Animal Care, and the Institutional Animal Care and Use Committee of New York Medical College. The animals were housed five per cage, and fed ad libitum, fresh tap water and commercial rodent pellets. Animal rooms were controlled at 24±2° C., with a relative humidity of 60±5%, and a 12 hr light/dark cycle (07:00-19:00 hr).

Animal Treatment:

Beginning at 16 weeks of age, disease progression of the mice was monitored weekly by assessing proteinuria. A cohort of mice, selected at 17 weeks of age, were served as the "asymptomatic normal" group (n=5). Constant proteinuria (>30 mg/dL) was detected for two consecutive occasions, and the kidney damage initiated (glomerular lesion>24%), the diseased mice were randomly divided into 5 groups (n=10). Group one animals were served as control (orally given vehicle only). Group 2 and 3 animals were given Meisoindigo suspension orally by gavage at doses of 25 mg/kg (0.09 mmol/kg) and 75 mg/kg (0.272 mmol/kg), once a day, 5 days per week for 25 weeks. Group 4 and 5 animals were given Natura suspension orally at equal molar doses as Meisoindigo above, i.e. 47 and 142 mg/kg, respectively, for the same period of time. Mice were monitored weekly for proteinuria until 44 weeks of age.

Assessment of Proteinuria:

Urine was manually expressed from each mouse on a weekly basis, collected into a sterile container and assayed for the presence of protein (specifically albumin), using a colorimetric method (Albustix Reagent Strips, Bayer Corporation, Elkhart, Ind.). Proteinuria evaluations were scored as follows: grade 0.5='trace' proteinuria; grade 1=about 30 mg/dL; grade 2=about 100 mg/dL; grade 3=about 300 mg/dL; and grade 4=more than 2000 mg/dL[33]. If mice achieved a grade 4 reading on two consecutive days, they would be euthanised.

Results

Figure 7:
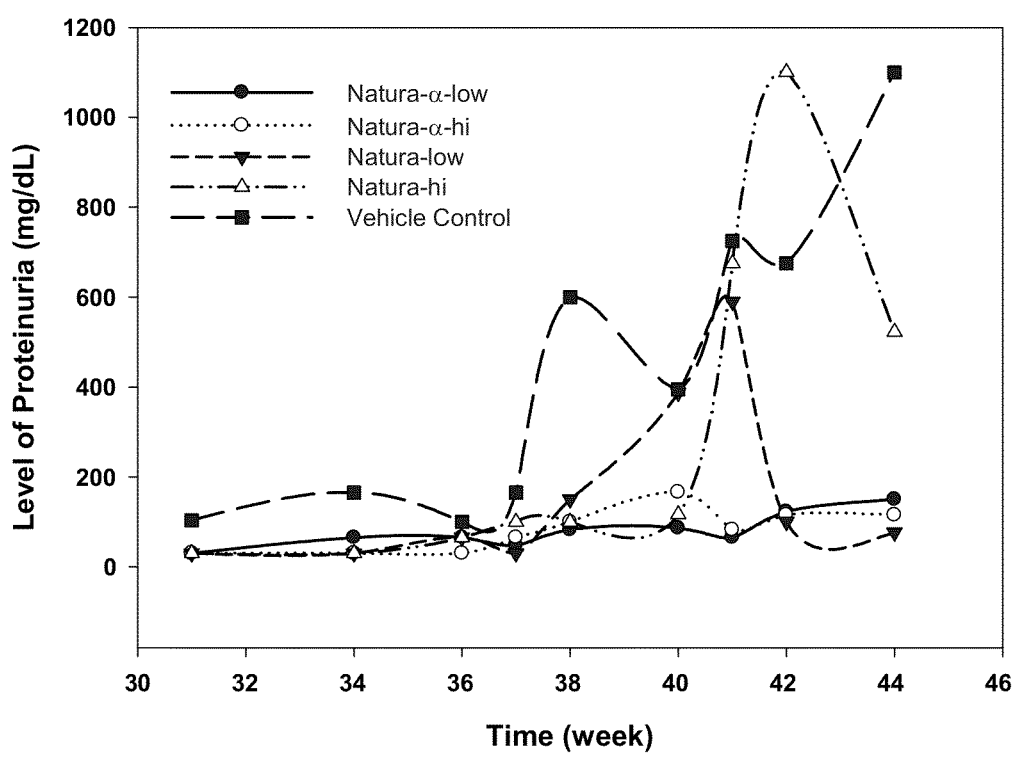
FIG. 7 shows the effects of Meisoindigo and Natura on proteinuria in NZB/W f1 mice. Beginning at 16 weeks of age, lupus progression of the mice was monitored weekly by assessing proteinuria. A cohort of mice, selected at 17 weeks of age, served as the 'asymptomatic normal' group. At week 19, proteinuria (>30 mg/dL) was detected at 2 consecutive occasions, and the expected kidney damage was initiated (glomerular lesion>24%), the diseased mice were randomly divided into 5 groups (n=10). Group one animals were served as control (orally given vehicle only). Group 2 and 3 animals were given Meisoindigo suspension orally by gavage at doses of 25 mg/kg (0.09 mmol/kg) and 75 mg/kg (0.272 mmol/kg), once a day, 5 days per week for 25 weeks. Group 4 and 5 animals were given Natura suspension orally at equal molar doses as Meisoindigo above, i.e. 47 and 142 mg/kg, respectively, for the same period of time. Mice were monitored weekly for proteinuria until 44 weeks of age. Urine was collected into a sterile container and assayed for the presence of protein (specifically albumin) using a colorimetric method (Albustix Reagent Strips, Bayer Corporation, Elkhart, Ind.).

The treatments of the animals with vehicle control or with Meisoindigo and Natura at two dose levels as described above began at week 19 when the animals developed proteinuria at 30 mg/dL and renal lesion initiated by histopathology. FIG. 7 shows dynamic changes with time in levels of proteinuria in mice with different treatment regimen. Proteinuria in mice treated with vehicle elevated at week 31, and sharply increased at week 38. In contrast, proteinuria in animals treated with both Meisoindigo and Natura at both dose levels essentially maintained at basil levels from week 31 to week 37, and only slightly elevated at week 38. With the disease progression, the proteinuria level in animals treated vehicle continuously and progressively increased and reached over 1000 mg/dL at week 44 whereas the levels in two Meisoindigo treated groups essentially maintained at stable lower level (150+100 mg/dL at dose of 25 mg/kg, and 115+127 mg/dL at dose of 75 mg/kg, respectively). In two Natura treated groups, the proteinuria levels were also significantly lower than the animals in vehicle treated group.

Example 7

Meisoindigo and Natura Remarkably Prevents Animal Death from Lupus in NZB/f1 Mice Methods:

The materials, animals, and animal treatments were the same as Example 6. Animal survival was observed and recorded during the treatment period daily.

Statistical Analysis:

All data are expressed as mean±SD. Statistical significance of any difference between the control and experimental groups were determined by the One Way ANOVA test with P value at least <0.05.

Figure 8:
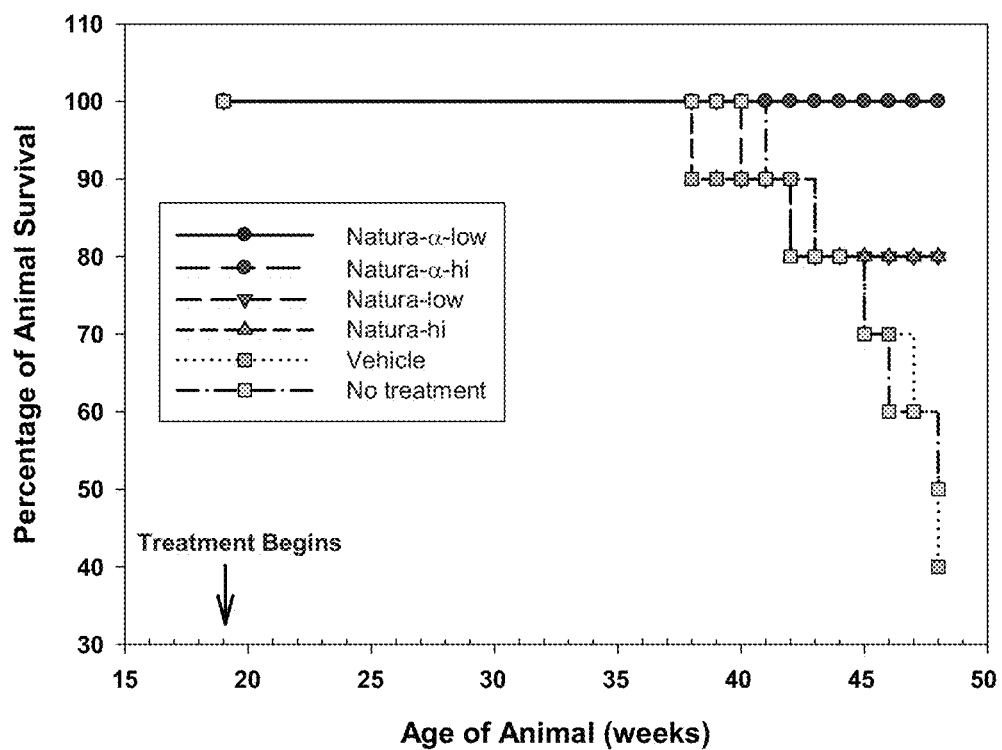
FIG. 8 shows the survival rates of NZB/W f1 treated with Meisoindigo (low: 0.09 mmol/kg and hi: 0.272 mmol/kg), or with equal mol doses of Natura or with vehicle or no treatment for 29 weeks. The animal survival was monitored daily. All animals in Meisoindigo treated groups survived whereas 80% animal survived in Natura treated groups, but only 40 to 50% animals survived in vehicle treated or not treated groups (p<0.001).

Results:

One characteristic of NZB/W mice is higher death rates as results of disease progression [37], thus we determined the survival rates of the mice in various treated groups and non-treatment group. The dynamic survival rates of the mice are shown in FIG. 8. Animals Began to die at week 38 in vehicle control group. After week 38, the death rates in the vehicle treatment group or non-treatment group were accelerated with time. At week 48, 60% of mice died in the vehicle treated group while 20% of the animals also died in two Natura treated groups. The survival rates in two Natura treated groups were found to be statistically significant higher than that of vehicle treated group (80% via 40%, p<0.001). Most importantly, all animals survived in two Meisoindigo treated groups (survival rate 100% via 40% in vehicle controlled group, p<0.001).

Example 8

Meisoindigo and Natura Effectively Prevents Renal Damage from Lupus in NZB/f1 Mice Methods:

The materials, animals, assessment of proteinuria were the same as Example 6.

Assessment of Renal Histopathology:

Kidneys were obtained from mice studied in Examples 6 and 7 after death to examine renal damages with the disease progression of lupus. One-half of a kidney was fixed by overnight immersion in 10% formaldehyde and paraffin embedded. To determine the extent of renal damage, sections were stained with H & E and periodic acid-Schiff (PAS), and scored for pathological changes by an independent pathologist. Glomerulopathy was scored on a 0 to 5 scale. Severity grades is as follows: 0=normal or within normal limits; 1=minimal or slight; 2=mild; 3=moderate; 4=marked; 5=severe [33]. In addition, the histological changes for mesangial proliferation, tubular dilation, protein cast deposition inside the tubules and inflammatory cell infiltration into the interstitium were also examined.

Figure 9:
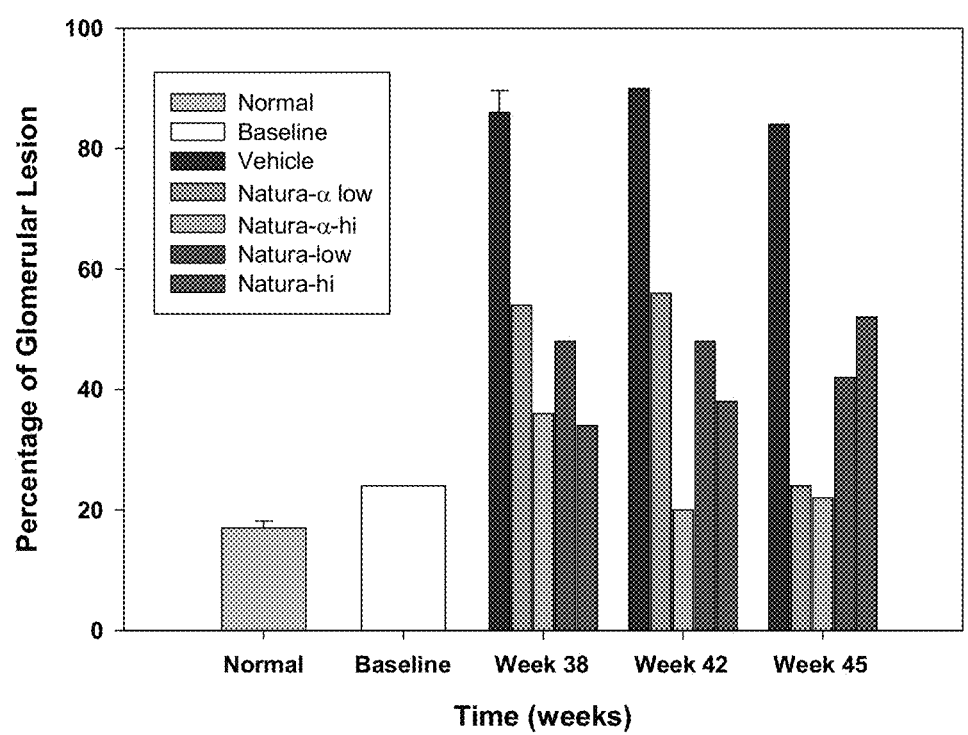
FIG. 9 shows changes in renal damages of NZB/W f1 mice treated with Meisoindigo (low: 0.09 mmol/kg; hi: 0.272 mmol/kg) or with equal mol doses of Natura or with vehicle. Kidneys were obtained from sacrificed mice during above treatments or from dead mice during the treatments. One-half of a kidney was fixed by overnight immersion in 10% formaldehyde and paraffin embedded. Kidney sections were stained with H & E and periodic acid-Schiff (PAS), and scored for pathological changes of glomeruli by an independent pathologist. Data represents mean±SD (when available). Glomerular lesion in vehicle treated animals reached maximal at week 38 and throughout the treatment period, and over 85% of glomeruli exhibited severe lesions. In comparison, approximately 54% glomerular lesion in lower dose of Meisoindigo treated group was observed at week 38, and week 42. However, this renal damage significant recovered at week 45, and it was almost back to the baseline level (24%). In the higher dose of the Meisoindigo treated group, the only moderate glomerular lesion was observed at week 38 (36% as compared with vehicle control 85%), and this damage recovered faster than that of lower dose group. The significant recovery to the baseline level occurred at week 42 (20% at week 42, and 22% at week 45 as compared with vehicle treated group 85%). Treatment of NZB/W f1 mice with two different doses of Natura also showed protective effects of renal damages from the lupus.

Results:

Normal levels of histological glomerular lesions were obtained from the kidneys of "asymptomatic mice" (week 17), and baseline glomerular renal lesion levels were obtained from mice at beginning of the treatment (week 19). Progressive renal lesions were initially examined when animals began to die at week 38 and throughout the treatment period to assess dynamic disease severity of lupus. As shown in FIG. 9, glomerular lesion in vehicle treated animals reached maximal at week 38 and throughout the treatment period, and over 85% of glomeruli exhibited severe lesions. In comparison, approximately 54% glomerular lesions in the lower dose of Meisoindigo treated group, was observed at week 38, and week 42. However, this renal damage significantly recovered at week 45, and it was almost back to the baseline level (24%). In the higher dose of Meisoindigo treated group, the only moderate glomerular lesions were observed at week 38 (36% as compared with vehicle control 85%), and this damage recovered even faster than that of lower dose group. Significant recovery to the baseline level occurred at week 42 (20% at week 42, and 22% at week 45 as compared with vehicle treated group 85%). Treatment of NZB/W f1 mice with two different doses of Natura also showed protection effects on renal damages from the lupus.

Figure 10:
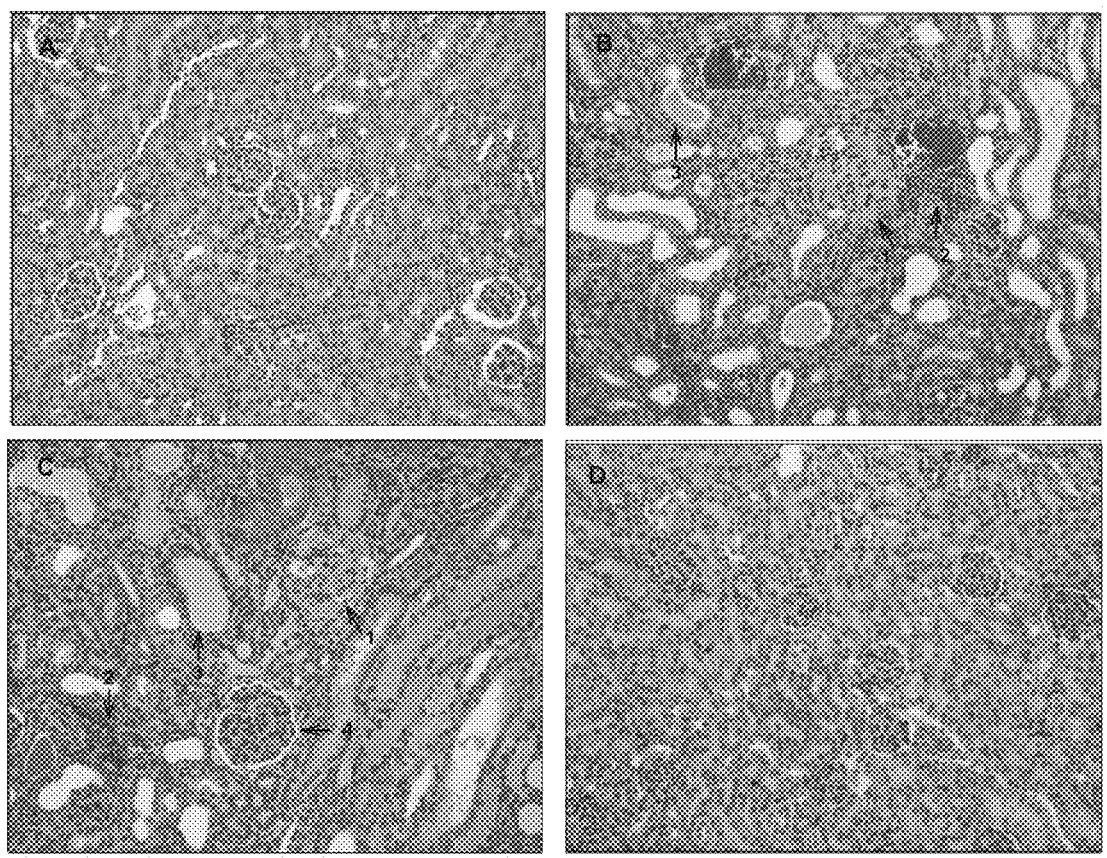
FIG. 10 depicts histopathological changes in kidneys of NZB/W f1 mice with various treatments: Panel A: from normal control mouse, shows normal histology of kidney; Panel B&C: from vehicle treated mouse, and D: from mouse treated with lower dose of Meisoindigo. Kidney sections from vehicle treated mice show significant 1) capillary lumen obliteration; 2) inflammatory cell infiltration; 3) tubular dilation with intra-tubular protein case deposition and, 4) proliferative glomerulonephritis (Panel B&C). These histopathological changes were remarked reduced or absent in Natura-treated mice (Panel D).

FIG. 10 depicts examples of histopathological changes in kidneys of NZB/W f1 mice with various treatments. Kidney sections from vehicle treated mice showed significant glomerulosclerosis, capillary lumen obliteration, proliferative glomerulonephritis, tubular dilation with intra-tubular protein case deposition and inflammatory cell infiltration. These histopathological changes were remarked reduced in Natura-treated mice.

Discussion and Conclusion:

The results of our study in this invention demonstrate that treatments of lupus in NZB/W f1 mice with Meisoindigo at daily doses of 25 mg/kg and 75 mg/kg, and Natura at equal molar doses for 29 weeks were very effective. These treatments significantly reduced levels of proteinuria, remarkably improved animal survival rates, preserved renal functions, prevented and reversed glomerular lesions. Since NZB/W mice develop nephritis, closely resembling that seen in human patients with lupus nephritis, our data strongly suggests the compounds in this invention will be useful in treating lupus.

REFERENCES

1. Bebo, B. F., Jr., Yong, T., Orr, E. L., and Linthicum, D. S. Hypothesis: a possible role for mast cells and their inflammatory mediators in the pathogenesis of autoimmune encephalomyelitis. J Neurosci Res, 45: 340-348, 1996.

2. Mennicken, F., Maki, R., de Souza, E. B., and Quirion, R. Chemokines and chemokine receptors in the CNS: a possible role in neuroinflammation and patterning. Trends Pharmacol Sci, 20: 73-78, 1999.
3. Watanabe, T. and Fan, J. Atherosclerosis and inflammation mononuclear cell recruitment and adhesion molecules with reference to the implication of ICAM-1/LFA-1 pathway in atherogenesis. Int J Cardiol, 66 Suppl 1: S45-53; discussion S55, 1998.
4. Sullivan, G. W., Sarembock, I. J., and Linden, J. The role of inflammation in vascular diseases. J Leukoc Biol, 67: 591-602, 2000.
5. Rogers, J. and Shen, Y. A perspective on inflammation in Alzheimer's disease. Ann N Y Acad Sci, 924: 132-135, 2000.
6. Tran T A, Ross J. S., Carlson J. A., and Mihm M. C., Jr. Mitotic cyclins and cyclin-dependent kinases in melanocytic lesions. Hum. Pathol. 29(10):1085-1090, 1988.
7. Fadare, O., Yi X., et al. Variations of mitotic index in normal and dysplastic squamous epithelium of the uterine cervix as a function of endometrial maturation. Mod. Pathol. 20(9):1000-1008.
8. Scholzen, T. and J. Gerdes. The ki-67 protein: from the known and the unknown. J. Cell Physiol. 182(3):311-22, 2000.
9. Schumann, R. R., Belka, C., Reuter, D., Lamping, N., Kirschning, C. J., Weber, J. R., and Pfeil, D. Lipopolysaccharide activates caspase-1 (interleukin-1-converting enzyme) in cultured monocytic and endothelial cells. Blood, 91: 577-584, 1998.
10. Yoza, B. K., Hu, J. Y., and McCall, C. E. Protein-tyrosine kinase activation is required for lipopolysaccharide induction of interleukin 1beta and NFkappaB activation, but not NFkappaB nuclear translocation. J Biol Chem, 271: 18306-18309, 1996.
11. Guha, M., O'Connell, M. A., Pawlinski, R., Hollis, A., McGovern, P., Yan, S. F., Stern, D., and Mackman, N. Lipopolysaccharide activation of the MEK-ERK1/2 pathway in human monocytic cells mediates tissue factor and tumor necrosis factor alpha expression by inducing Elk-1 phosphorylation and Egr-1 expression. Blood, 98: 1429-1439, 2001.
12. Guha, M. and Mackman, N. LPS induction of gene expression in human monocytes. Cell Signal, 13: 85-94, 2001.
13. Wang, E., Ma, W. J., Aghajanian, C., and Spriggs, D. R. Posttranscriptional regulation of protein expression in human epithelial carcinoma cells by adenine-uridine-rich elements in the 3'-untranslated region of tumor necrosis factor-alpha messenger RNA. Cancer Res, 57: 5426-5433, 1997.
14. Dean, J. L., Wait, R., Mahtani, K. R., Sully, G., Clark, A. R., and Saklatvala, J. The 3' untranslated region of tumor necrosis factor alpha mRNA is a target of the mRNA-stabilizing factor HuR. Mol Cell Biol, 21: 721-730, 2001.
15. Osman, F., Jarrous, N., Ben-Asouli, Y., and Kaempfer, R. A cis-acting element in the 3'-untranslated region of human TNF-alpha mRNA renders splicing dependent on the activation of protein kinase PKR. Genes Dev, 13: 3280-3293, 1999.
16. Palladino, M. A., Bahjat, F. R., Theodorakis, E. A., and Moldawer, L. L. Anti-TNF-alpha therapies: the next generation. Nat Rev Drug Discov, 2: 736-746, 2003.
17. Feldmann, M. Pathogenesis of arthritis: recent research progress. Nat Immunol, 2: 771-773, 2001.
18. Tsuchiya, S., Yamabe, M., Yamaguchi, Y., Kobayashi, Y., Konno, T., and Tada, K. Establishment and characterization of a human acute monocytic leukemia cell line (THP-1). Int J Cancer, 26: 171-176, 1980.
19. Liu, J. H., Wei, S., Burnette, P. K., Gamero, A. M., Hutton, M., and Djeu, J. Y. Functional association of TGF-beta receptor II with cyclin B. Oncogene, 18: 269-275, 1999.
20. Wang, L. G., Liu, X. M., Kreis, W., and Budman, D. R. Down-regulation of prostate-specific antigen expression by finasteride through inhibition of complex formation between androgen receptor and steroid receptor-binding consensus in the promoter of the PSA gene in LNCaP cells. Cancer Res, 57: 714-719, 1997.
21. Wang, L. G., Liu, X. M., Wikiel, H., and Bloch, A. Activation of casein kinase II in ML-1 human myeloblastic leukemia cells requires IGF-1 and transferrin. J Leukoc Biol, 57: 332-334, 1995.
22. Kong, M., Barnes, E. A., Ollendorff, V., and Donoghue, D. J. Cyclin F regulates the nuclear localization of cyclin B1 through a cyclin-cyclin interaction. Embo J, 19: 1378-1388, 2000.
23. McGovern, S. L. and Shoichet, B. K. Kinase inhibitors: not just for kinases anymore. J Med Chem, 46: 1478-1483, 2003.
24. Group, C. Phase III clinical trials of Meisoindigo on the treatment of chronic myeloid leukemia. J. Chinese Hematology, 18: 69-72, 1997.
25. Haversen, L., Ohlsson, B. G., Hahn-Zoric, M., Hanson, L. A., and Mattsby-Baltzer, I. Lactoferrin down-regulates the LPS-induced cytokine production in monocytic cells via NF-kappa B. Cell Immunol, 220: 83-95, 2002.
26. Tang, X., Fenton, M. J., and Amar, S. Identification and functional characterization of a novel binding site on TNF-alpha promoter. Proc Natl Acad Sci USA, 100: 4096-4101, 2003.
27. Girolomoni, G., Pastore, S., Albanesi, C., and Cavani, A. Targeting tumor necrosis factor-alpha as a potential therapy in inflammatory skin diseases. Curr Opin Investig Drugs, 3: 1590-1595, 2002.
28. Santiago-Raber, M. L., et al., Genetic basis of murine lupus. Autoimmun Rev, 2004. 3(1): p. 33-9.
29. Foster, M. H., Relevance of systemic lupus erythematosus nephritis animal models to human disease. Semin Nephrol, 1999. 19(1): p. 12-24.
30. Reilly, C. M. and G. S. Gilkeson, Use of genetic knockouts to modulate disease expression in a murine model of lupus, MRL/lpr mice. Immunol Res, 2002. 25(2): p. 143-53.
31. Liu, J., et al., Genomic view of systemic autoimmunity in MRLlpr mice. Genes Immun, 2006. 7(2): p. 156-68.
32. Shlomchik, M. J., J. E. Craft, and M. J. Mamula, From T to B and back again: positive feedback in systemic autoimmune disease. Nat Rev Immunol, 2001. 1(2): p. 147-53.
33. Hutloff, A., et al., Involvement of inducible costimulator in the exaggerated memory B cell and plasma cell generation in systemic lupus erythematosus. Arthritis Rheum, 2004. 50(10): p. 3211-20.
34. Ramos-Barron, A., et al., Prevention of murine lupus disease in (NZB×NZW)F1 mice by sirolimus treatment. Lupus, 2007. 16(10): p. 775-81.
35. Warner, L. M., L. M. Adams, and S. N. Sehgal, Rapamycin prolongs survival and arrests pathophysiologic changes in murine systemic lupus erythematosus. Arthritis Rheum, 1994. 37(2): p. 289-97.
36. Lui, S. L., et al., Rapamycin prevents the development of nephritis in lupus-prone NZB/W F1 mice. Lupus, 2008. 17(4): p. 305-13.

37. Reddy, P. S., et al., Mapping similarities in mTOR pathway perturbations in mouse lupus nephritis models and human lupus nephritis. Arthritis Res Ther, 2008. 10(6): p. R127.

What is claimed is:

1. A method of treating an animal with lupus nephritis, the method comprising the step of administering to the animal in need of such treatment at least one compound selected from the group of: Meisoindigo, tri-acetylated glyco-Meisoindigo (pro-drug) or 1-(β-D-O-triacetyl-xylopyranosyl)-isoindigo, shown as Formulas (IV), (V), and (VI) respectively,

FORMULA (IV)

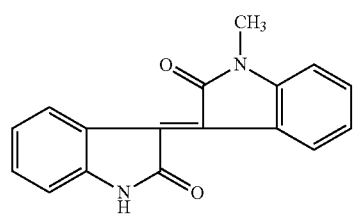

FORMULA (V)

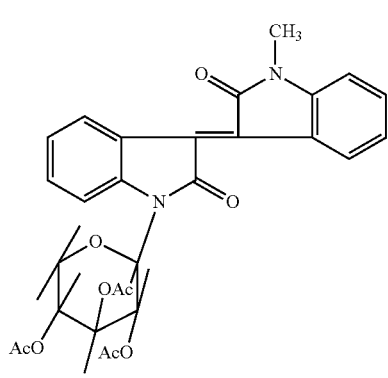

FORMULA (VI)

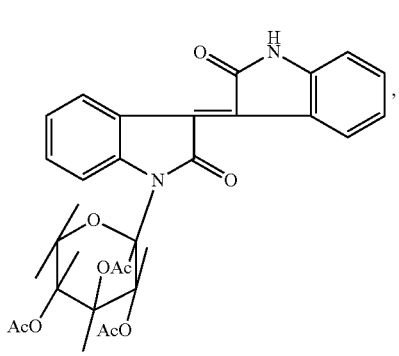

wherein the compound is administered in an amount sufficient to treat lupus nephritis.

2. The method according to claim 1, wherein the amount administered is sufficient to inhibit pro-inflammatory cytokine expression and/or stimulate anti-inflammatory cytokine expression, but the amount is less than sufficient to substantially inhibit cyclin dependent kinases.

3. The method according to claim 1, wherein the amount administered is less than about 0.36 mmol/kg per day.

4. The method according to claim 3, wherein the compound administered is Meisoindigo and the amount administered is less than about 100 mg/kg per day.

5. The method according to claim 3, wherein the amount administered is between 0.036 mmol/kg and 0.288 mmol/kg per day.

6. The method according to claim 4, wherein the amount administered is between 10 mg and 80 mg per day.

7. The method according to claim 1, wherein the animal is a human.

8. The method according to claim 2, wherein the compound is administered in an amount sufficient to inhibit cytokine IL-1α, β, IL-2, IL-3, IL-6, IL-7, IL-9, IL-12, IL-17, IL-18, TNF-α, LT, LIF, Oncostatin, or IFNc1α, β, γ.

9. The method according to claim 2, where the compound is administered in an amount sufficient to stimulate expression of cytokine IL-4, IL-10, IL-11, W-13 or TGFβ.

10. The method according to claim 2, where the compound is administered in an amount sufficient to modulate cytokines TNF-α, IL-1β, IL-6, and IL-10.

11. The method according to claim 1, where the compound is administered in an amount sufficient to reduce proteinuria levels and/or sufficient to modulate a humoral response.

12. The method according to claim 11, wherein modulation of a humoral response includes a decrease in total IgG antibody within the animal.

13. A method of treating lupus nephritis, the method comprising the step of administering to an animal in need of such treatment at least a first and a second compound, wherein the first compound is selected from the group of: Meisoindigo, tri-acetylated glyco-Meisoindigo (pro-drug) or 1-(β-D-O-triacetyl-xylopyranosyl)-isoindigo, shown as Formulas (IV), (V), and (VI) respectively,

FORMULA (IV)

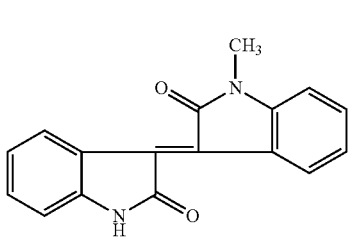

FORMULA (V)

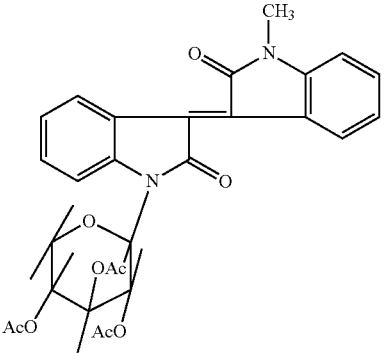

wherein the second compound is selected from the group consisting of: anti-inflammatory agent, corticosteroid, immune suppressant, or biologic drug; and wherein the first compound is administered in an amount sufficient to treat lupus nephritis.

14. The method according to claim 13, wherein the first compound is administered in an amount sufficient to inhibit pro-inflammatory cytokine expression and/or stimulate anti-inflammatory cytokine expression, but the amount is less than sufficient to substantially inhibit cyclin dependent kinases.

15. The method according to claim 13, wherein the compounds are administered concurrently within a single composition.

16. The method according to claim 13, wherein the compounds are administered sequentially.

17. The method according to claim 13, wherein the second compound is selected from the group of: ibuprofen, corticosteroid, methotrexate, or BLyS-specific inhibitors.

18. The method according to claim 17, wherein the BLyS-specific inhibitor is belimumab.

19. The method according to claim 13, wherein the first compound is administered in an amount less than about 0.36 mmol/kg per day.

20. The method of claim 17, wherein the first compound is administered in an amount between 0.036 mmol/kg and 0.288 mmol/kg per day.

21. The method according to claim 13, wherein the animal is a human.

22. The method according to claim 13, wherein the first compound is administered in an amount sufficient to inhibit cytokine IL-1α, β, IL-2, IL-3, IL-6, IL-7, IL-9, IL-12, IL-17, IL-18, TNF-α, LT, LIF, Oncostatin, or IFNc1α, β, γ; and/or sufficient to stimulate expression of cytokine IL-4, IL-10, IL-11, W-13 or TGFβ.

23. The method according to claim 13, where the first compound is administered in an amount sufficient to modulate cytokines TNF-α, IL-1β, IL-6, and IL-10.

24. The method according to claim 13, where the first compound is administered in an amount sufficient to reduce proteinuria levels and/or sufficient to modulate a humoral response.

25. The method according to claim 24, wherein modulation of a humoral response includes a decrease in total IgG antibody within the animal.

26. A composition for treating lupus nephritis, the compositions comprising an active compound, an agent, and a pharmaceutically acceptable carrier, wherein the active compound is selected from the group of: Meisoindigo, tri-acetylated glyco-Meisoindigo (pro-drug) or 1-(β-D-O-triacetyl-xylopyranosyl)-isoindigo, shown as Formulas (IV), (V), and (VI) respectively, and the agent is selected from the group consisting of: an anti-inflammatory agent, corticosteroid agent, immune suppressant agent, or a biologic drug.

27. The composition of claim 26, wherein the anti-inflammatory agent is ibuprofen, the immune suppressant agent is methotrexate, and the biologic drug is a BLyS-specific inhibitor.

28. The composition of claim 27, wherein the BLyS-specific inhibitor is belimumab.

29. A method of treating an animal with nephritis, the method comprising the step of administering to the animal in need of such treatment at least one compound selected from the group of: Meisoindigo, tri-acetylated glyco-Meisoindigo (pro-drug) or 1-(β-D-O-triacetyl-xylopyranosyl)-isoindigo, shown as Formulas (IV), (V), and (VI) respectively,

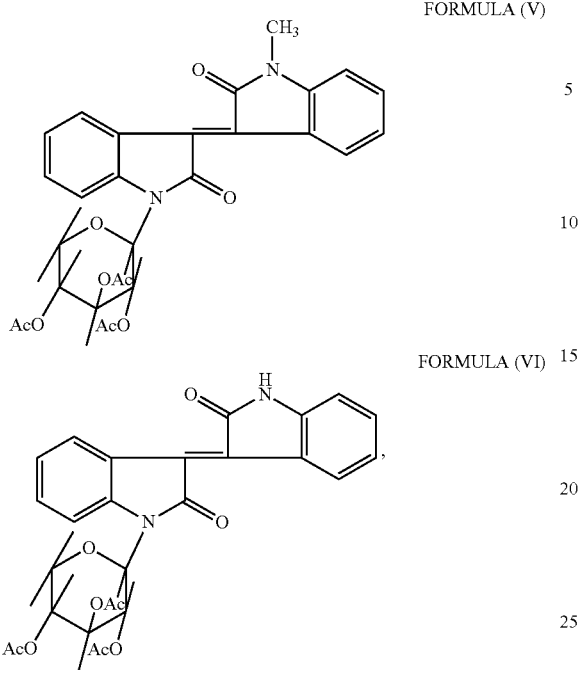
wherein the compound is administered is in an amount sufficient to treat nephritis.
30. The method of claim 27, wherein the nephritis is glomerulonephritis.
* * * * *